United States Patent
Yoshida

(10) Patent No.: US 11,058,361 B2
(45) Date of Patent: Jul. 13, 2021

(54) SIGNAL PROCESSING APPARATUS, IMAGING APPARATUS, AND SIGNAL PROCESSING METHOD

(71) Applicant: TOSHIBA MEDICAL SYSTEMS CORPORATION, Otawara (JP)

(72) Inventor: Takami Yoshida, Kawasaki (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 1382 days.

(21) Appl. No.: 14/929,527

(22) Filed: Nov. 2, 2015

(65) Prior Publication Data

US 2016/0128643 A1     May 12, 2016

(30) Foreign Application Priority Data

Nov. 6, 2014 (JP) .............................. JP2014-226259
Oct. 29, 2015 (JP) .............................. JP2015-212542

(51) Int. Cl.
  *A61B 5/00* (2006.01)
  *A61B 5/0245* (2006.01)
  (Continued)

(52) U.S. Cl.
  CPC ............ *A61B 5/7285* (2013.01); *A61B 5/352* (2021.01); *A61B 5/0042* (2013.01); *A61B 5/0245* (2013.01);
  (Continued)

(58) Field of Classification Search
  CPC ... A61B 5/0456; A61B 5/7285; A61B 5/0245; A61B 5/055; A61B 5/7289;
  (Continued)

(56) References Cited

U.S. PATENT DOCUMENTS 5,987,348 A    11/1999   Fischer et al.
8,290,575 B2   10/2012   Tarassenko et al.
(Continued)

FOREIGN PATENT DOCUMENTS

JP      6-237909 A    8/1994
JP      2004-89314 A    3/2004
(Continued)

OTHER PUBLICATIONS

Johannes W. Krug et al., "ECG-based Gating in Ultra High Field Cardiovascular Magnetic Resonance Using an Independent Component Analysis Approach", Journal of Cardiovascular Magnetic Resonance, 2013, 13 pages.
(Continued)

*Primary Examiner* — Baisakhi Roy
(74) *Attorney, Agent, or Firm* — Oblon, McClelland, Maier & Neustadt, L.L.P.

(57) ABSTRACT

In one embodiment, a signal processing apparatus includes a storage circuit and processing circuitry configured to (a) generate detection parameters for detecting a specific signal included in a biosignal relevant to a heartbeat, based on a waveform of the biosignal, (b) store the detection parameters in the storage circuit, (c) detect the specific signal by using the detection parameters, and (d) generate a synchronization signal for performing heartbeat synchronization imaging based on the specific signal.

14 Claims, 22 Drawing Sheets

(51) Int. Cl.
*A61B 5/0456* (2006.01)
*A61B 5/352* (2021.01)
*A61B 6/00* (2006.01)
*A61B 5/055* (2006.01)
*A61B 5/35* (2021.01)
*A61B 5/318* (2021.01)

(52) U.S. Cl.
CPC ............ *A61B 5/055* (2013.01); *A61B 5/318* (2021.01); *A61B 5/35* (2021.01); *A61B 5/7246* (2013.01); *A61B 5/7289* (2013.01); *A61B 6/541* (2013.01)

(58) Field of Classification Search
CPC ............ A61B 5/04525; A61B 5/04011; A61B 5/04012; A61B 5/0402; A61B 5/042; A61B 5/02; A61B 5/0205; A61B 5/04023; A61B 5/35; A61B 5/352; A61B 5/02411
See application file for complete search history.

(56) References Cited

U.S. PATENT DOCUMENTS

| | | | |
|---|---|---|---|
| 8,401,624 B2 | 3/2013 | Govari | |
| 8,532,762 B2 | 9/2013 | Cazares et al. | |
| 2003/0083586 A1* | 5/2003 | Ferek-Petric | A61B 5/04011 600/512 |
| 2003/0229289 A1* | 12/2003 | Mohler | A61B 5/725 600/508 |
| 2004/0073124 A1* | 4/2004 | Axel | A61B 5/04525 600/509 |
| 2007/0265540 A1 | 11/2007 | Fuwamoto et al. | |
| 2009/0275850 A1* | 11/2009 | Mehendale | A61B 5/35 600/523 |
| 2012/0184858 A1* | 7/2012 | Harlev | A61B 5/0402 600/484 |
| 2014/0081162 A1 | 3/2014 | Snell et al. | |
| 2015/0178631 A1* | 6/2015 | Thomas | G06K 9/0053 706/12 |
| 2015/0362574 A1* | 12/2015 | Wu | G01R 33/4835 324/322 |
| 2016/0270670 A1* | 9/2016 | Oz | A61B 5/02405 |

FOREIGN PATENT DOCUMENTS

| | | |
|---|---|---|
| JP | 2007-301101 A | 11/2007 |
| JP | 2001-500777 A | 1/2011 |
| JP | 5207172 B2 | 6/2013 |
| JP | 2015-208461 A | 11/2015 |
| JP | 2015-213714 A | 12/2015 |
| WO | WO 2004/008960 A1 | 1/2004 |

OTHER PUBLICATIONS

Seong-Beom Cho et al,, "Implementation of Novel ECG Compression Algorithm Using Template Matching", Int. Conf. Computing and Convergence Technology, Dec. 2012, pp. 305-308.

Japanese Office Action dated Aug. 27, 2019, in Patent Application No. 2015-212542, 3 pages.

* cited by examiner

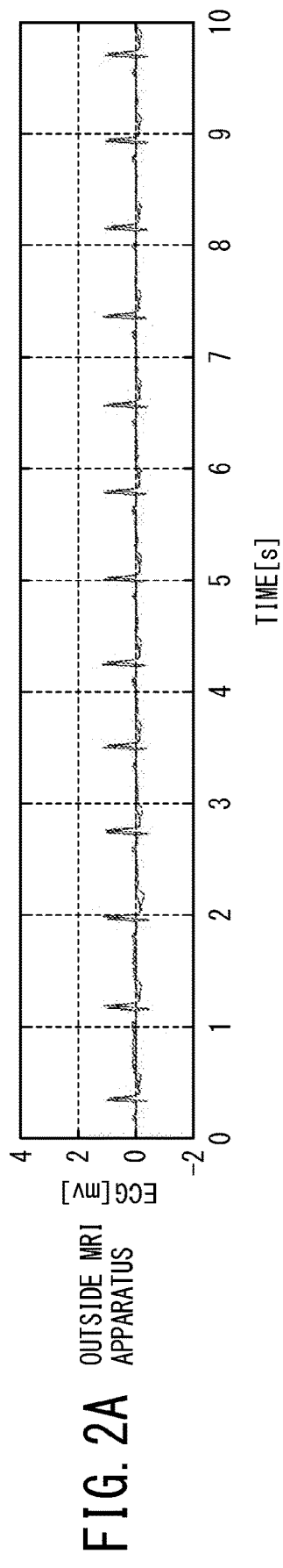
FIG. 2A OUTSIDE MRI APPARATUS
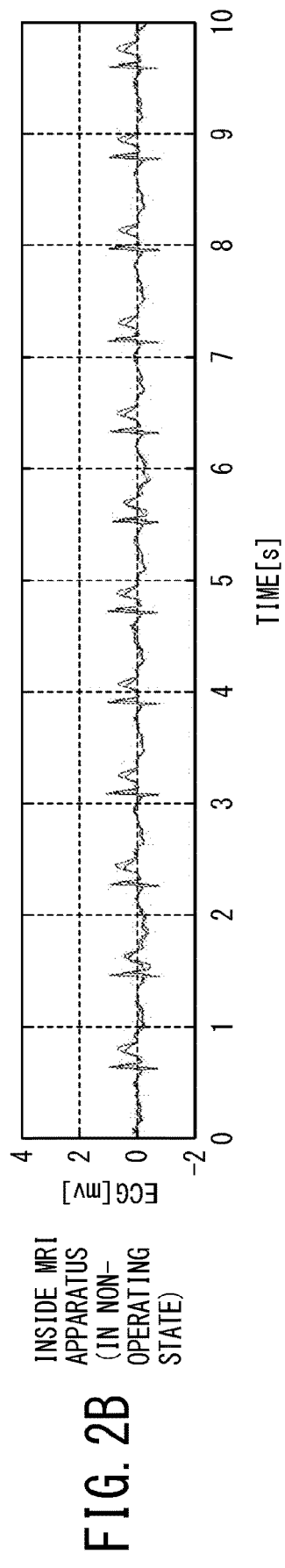
FIG. 2B INSIDE MRI APPARATUS (IN NON-OPERATING STATE)
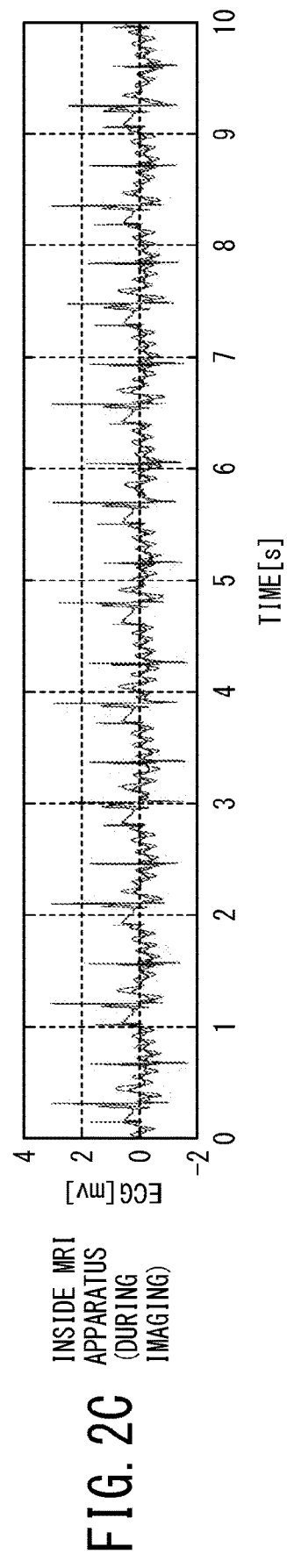
FIG. 2C INSIDE MRI APPARATUS (DURING IMAGING)

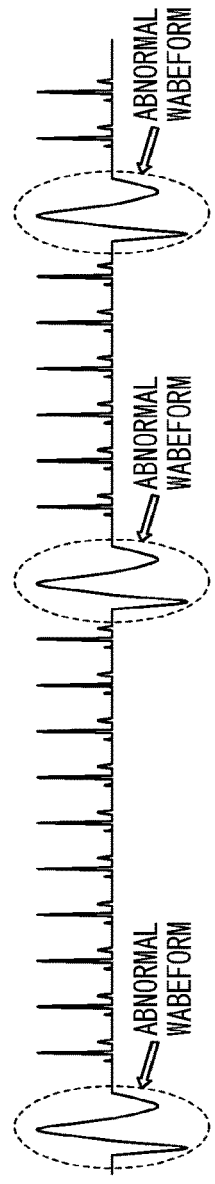
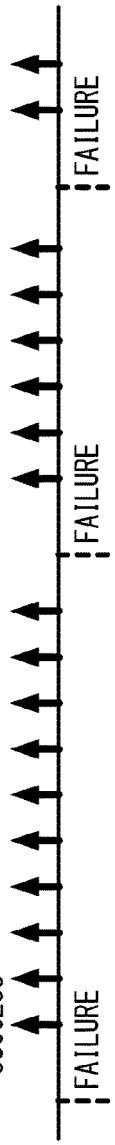
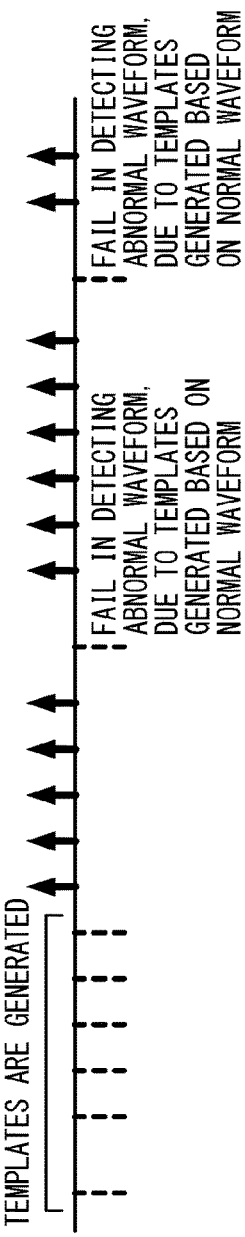

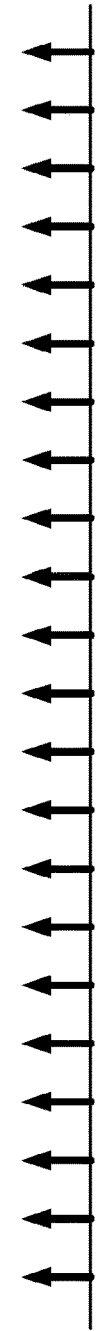

NO NOISE

NOISE IS SUPERIMPOSED

SIGNAL PROCESSING APPARATUS, IMAGING APPARATUS, AND SIGNAL PROCESSING METHOD

CROSS-REFERENCE TO RELATED APPLICATIONS

This application claims the benefit of priority of Japanese Patent Application No. 2014-226259, filed on Nov. 6, 2014, and Japanese Patent Application No. 2015-212542, filed on Oct. 29, 2015, the entire contents of each of which are incorporated herein by reference.

FIELD

Embodiments described herein relate generally to a signal processing apparatus, an imaging apparatus, and a signal processing method.

BACKGROUND

An electrocardiograph is a device whose electrodes are set on a biological body to measure an electric potential difference between the electrodes. A signal measured by an electrocardiograph is referred to as an ECG (electrocardiogram) signal and is widely used in the medical field. The ECG signal includes waveforms such as a P-wave, an R-wave, a QRS complex wave, and a T-wave. Since these waveforms are used for a synchronization signal of a medical diagnosis device capable of electrocardiographic synchronization imaging in addition to diagnosis of various cardiac diseases, automatic detection of such waveforms is important in terms of industrial applications.

In cardiac diagnosis using images obtained by an MRI (Magnetic Resonance Imaging) apparatus as an example, imaging is performed in synchronization with the timing of systole and/or diastole of a heart by using a synchronization signal (which is also referred to as a trigger signal) detected from an ECG signal. Such imaging is referred to as ECG synchronization imaging.

When ECG synchronization imaging is performed, a trigger signal is generated by detecting a specific waveform in an ECG signal, and start and end of imaging are controlled based on the timing synchronized with this trigger signal. Especially, a trigger signal is generated by detecting an R-wave in an ECG signal in many cases. In such cases, imaging is sometimes performed immediately after the timing of an R-wave and thus the delay time from detection of an R-wave to generation of a trigger signal is preferably as short as possible.

In addition, when a specific signal is detected from an ECG signal, it is necessary to detect a trigger signal with low delay and high accuracy not only from a normal waveform of an ECG signal but also from an abnormal waveform of an ECG signal. A patient, who undergoes a cardiac examination with an image diagnostic apparatus such as an MRI apparatus, is suspected to have a certain cardiac disease in many cases and thus ECG signals as the detection target of each trigger signal include an abnormal waveform in some cases. Since systole and diastole of a heart is repeated even in the case of such an abnormal waveform, it is necessary to infallibly detect a trigger signal with short delay time from an abnormal waveform included in ECG signals in order to perform imaging synchronized with systole and/or diastole of a heart.

Meanwhile, since application of pulsed gradient magnetic fields and pulsed RF (Radio Frequency) magnetic fields is included in imaging with the use of an MRI apparatus, noise which dynamically changes due to the application of the above magnetic fields is superimposed on ECG signals. Accordingly, it is also necessary to infallibly detect a synchronization signal from an ECG signal on which such noise is superimposed.

BRIEF DESCRIPTION OF THE DRAWINGS

In the accompanying drawings:

FIG. 2A to FIG. 2C are schematic diagrams, each of which shows an ECG signal with noise superimposed on and difficulty in detecting an R-wave from such an ECG signal;

FIG. 12A to FIG. 12E are timing charts for explaining the effect of the ECG signal processing apparatus of the second embodiment, in comparison with conventional detection methods;

FIG. 15A to FIG. 15E are timing charts showing examples of operations performed by the ECG signal processing apparatus of the third embodiment;

DETAILED DESCRIPTION

In one embodiment, a signal processing apparatus includes a storage circuit and processing circuitry configured to (a) generate detection parameters for detecting a specific signal included in a biosignal relevant to a heartbeat, based on a waveform of the biosignal, (b) store the detection parameters in the storage circuit, (c) detect the specific signal by using the detection parameters, and (d) generate a synchronization signal for performing heartbeat synchronization imaging based on the specific signal.

ECG signal processing apparatuses, ECG synchronization imaging apparatuses (imaging apparatuses), and ECG signal processing methods according to embodiments of the present invention will be described with reference to the accompanying drawings. Note that components of the same reference number operate or function in the same way in the following embodiments and thus duplicate explanation is omitted.

First Embodiment

Figure 1A:
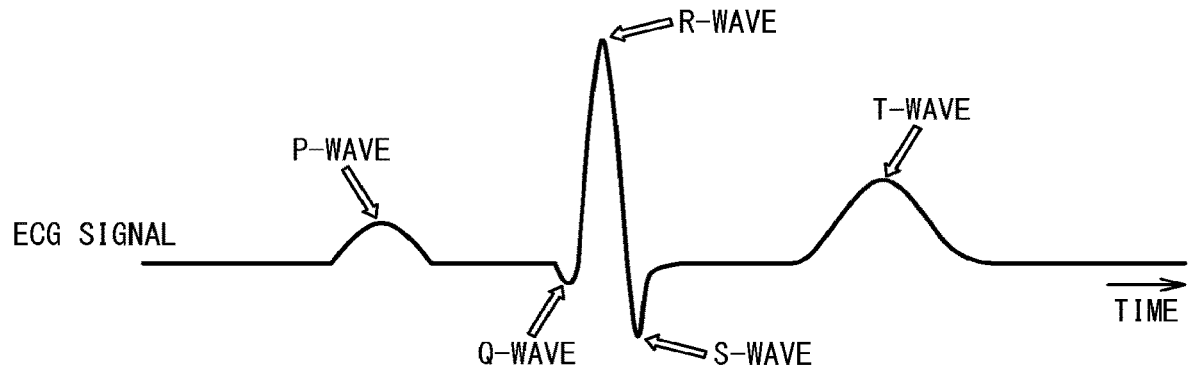
FIG. 1A is a schematic diagram showing an ECG signal which is a detection target of the ECG waveform processing apparatus of the first embodiment.

FIG. 1A is a schematic diagram showing an ECG signal which is a detection target of the ECG waveform processing apparatus 1 of the first embodiment. As shown in FIG. 1A, the ECG signal includes specific waveforms such as a P-wave, an R-wave, and a T-wave.

In each of the following embodiments, an example of detecting an R-wave among the specific waves will be explained. However, an example of detecting an R-wave is only one aspect and the ECG waveform processing apparatus 1, 1a, 1b, 1c, 1d, and 1e of the following embodiments can detect waveforms other than an R-wave (such as a P-wave and a T-wave, for example).

Figure 1B:
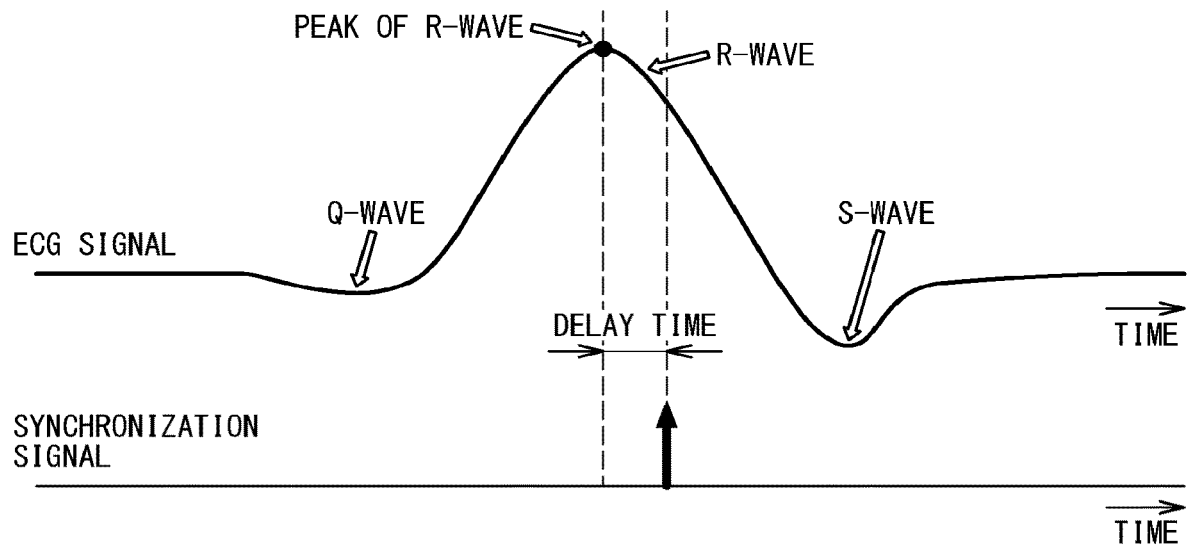
FIG. 1B is a schematic diagram obtained by magnifying the vicinity of an R-wave in FIG. 1A.

FIG. 1B is a schematic diagram obtained by magnifying the vicinity of an R-wave in FIG. 1A. In FIG. 1B, the time interval from the peak of the R-wave to the heartbeat synchronization signal is defined as a delay time. Hereinafter, the heartbeat synchronization signal is simply referred to as a synchronization signal. As an ECG synchronization imaging apparatus 200 (i.e., imaging apparatus 200) capable of imaging in synchronization with a heartbeat, for example, a CT (Computed Tomography) apparatus and an MRI (Magnetic Resonance Imaging) apparatus are included.

The ECG synchronization imaging apparatus 200 uses an imaging technique (ECG synchronization imaging technique) in which a start timing of data acquisition is determined with reference to a generation timing of an R-wave, for example. The ECG synchronization imaging apparatus 200 acquires the synchronization signal corresponding to the timing or position of the R-wave, and determines the start timing of data acquisition based on the acquired synchronization signal as a reference. Depending on a purpose of imaging, acquisition of imaging data is needed immediately after an R-wave. Therefore, time from detecting the arrival of an R-wave from an ECG signal to generation of a synchronization signal (i.e., a delay time) is needed to be shortened.

For example, in an MRI apparatus, various techniques of non-contrast MRA (Magnetic Resonance Angiography) such as an FBI (Fresh Blood Imaging) technique, a Time-SLIP (Time-Spatial Labeling Inversion Pulse) technique are used. In the data acquisition of the FBI technique, the MRI apparatus can obtain vascular images depicting an artery by (a) controlling the data acquisition timing with reference to a synchronization signal to obtain diastole images and systole images and (b) calculating subtraction images between the diastole images and the systole images, for example. In the data acquisition of the Time-SLIP technique, the MRI apparatus can obtain blood flow images by, for example, controlling the timing of data acquisition and the timing of applying a labeling pulse with reference to a synchronization signal.

As mentioned above, an MRI apparatus controls the timing of data acquisition and the timing of applying various pulses based on the synchronization signals generated from ECG signals as a reference. Since these timings are immediately after an R-wave in many cases, it is desirable that this delay time is as short as possible. Incidentally, the above-mentioned techniques are only examples. Needless to say, an MRI apparatus acquires imaging data with reference to a synchronization signal in other imaging such as contrast-enhanced imaging and various types of imaging in which an imaging target is an organ such as a heart.

As is clear from FIG. 1A, an R-wave generally shows the largest amplitude of the waveforms included in an ECG signal. However, even such an R-wave is susceptible to the influence of noise during imaging with the use of an MRI apparatus, which makes it difficult to detect the R-wave. FIG. 2A to FIG. 2C are schematic diagrams showing the above-described difficulty in detecting an R-wave. In each of FIG. 2A, FIG. 2B, and FIG. 2C, signals of respective two channels outputted from an electrocardiograph are superimposed.

FIG. 2A shows an example of an ECG signal observed in a condition under which an object such as a patient is outside an MRI apparatus. In FIG. 2A, noise is comparatively small and an R-wave is distinctly indicated.

FIG. 2B shows an example of an ECG signal observed in a condition under which an object is inside a bore of an MRI apparatus. In the case of FIG. 2B, the MRI apparatus is in a non-operating state (i.e., in a state where imaging is not performed) and only a static magnetic field is applied on the object. Although a T-wave subsequent to an R-wave in FIG. 2B is larger than that in FIG. 2A due to influence of blood flowing under the static magnetic field, dynamic noise is not so large in the case of FIG. 2B.

FIG. 2C shows an example of an ECG signal observed during imaging. In FIG. 2C, it can be recognized that large noise is superimposed on each ECG signal due to influence of gradient magnetic fields and RF pulses applied during imaging.

Note that an MRI apparatus acquires imaging data by executing a pulse sequence in which various imaging conditions such as intensity and application timings of gradient magnetic fields and RF pulses are determined. Further, an imaging sequence from the start of a pulse sequence to the completion of acquisition of predetermined imaging data by repeating necessary number of TR (Repetition Time) is often referred to as a protocol.

Hereafter, each of the following three phrases for describing a state of an MRI apparatus including "in an operating state", "during imaging", and "in a state where imaging is performed" means a period during which a pulse sequence is applied.

By contrast, each of the following three phrases for describing a state of an MRI apparatus including "in a non-operating state", "during suspension", and "in a state where imaging is not performed" means a period during which a pulse sequence is not applied.

For example, a period before start of the first protocol, which is included in a series of examinations, corresponds to the above-described "in an non-operating state", "during suspension", and "in a state where imaging is not performed". A period between one protocol and the next protocol also corresponds to the above-described "in an non-operating state", "during suspension", and "in a state where imaging is not performed".

Further, a period during which any gradient magnetic field or RF pulse is not applied may exist in one TR included in a pulse sequence. Such a period may be treated as the above-described "in a non-operating state", "during suspension", or "in a state where imaging is not performed".

Figure 3:
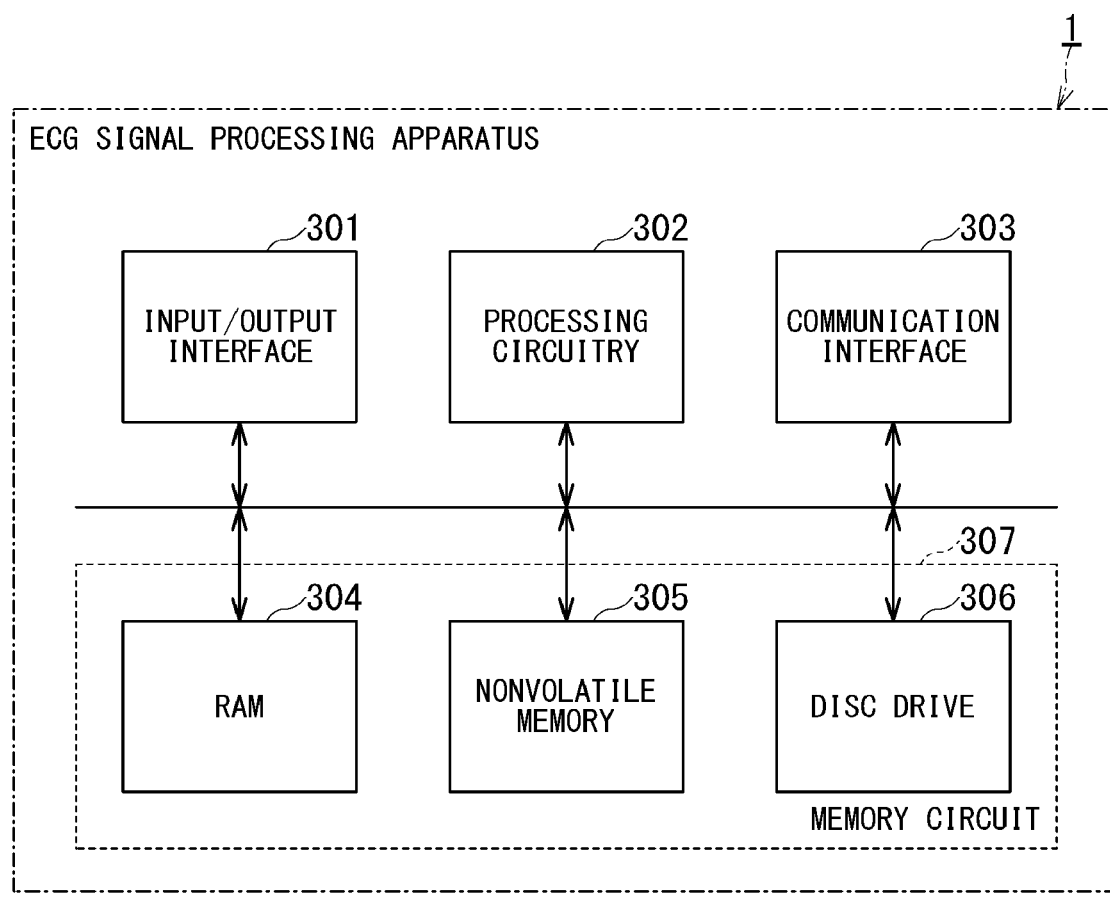
FIG. 3 is a block diagram showing an example of hardware configuration of the ECG signal processing apparatus of the first embodiment.

FIG. 3 is a block diagram showing an example of hardware configuration of the ECG signal processing apparatus 1. The ECG signal processing apparatus 1 includes an input/output interface 301, processing circuitry 302, a communication interface 303, and a memory circuit 307. The memory circuit 307 includes a RAM (Random Access Memory) 304, a nonvolatile memory 305, and a disc drive 306.

The nonvolatile memory 305 of the memory circuit 307 is a storage device such as a hard disc and a flash memory, and stores various programs and various types of data.

The processing circuitry 302 includes one or plural processors, for example. The above-described term "processor" includes, for instance, a processor such as a special-purpose or general-purpose CPU (Central Processing Unit), or a special-purpose or general-purpose signal processor.

The processor of the processing circuitry 302 implements various functions of the ECG signal processing apparatus 1 as described below by software processing, i.e., by reading one or plural programs from the nonvolatile memory 305 to the RAM 304 and executing the programs. Additionally, the processor of the processing circuitry 302 may read in programs stored in a recording medium such as a magnetic disc, an optical disc, and a USB (Universal Serial Bus) memory via the disc drive 306 or the input/output interface 301, aside from the programs stored in the nonvolatile memory 305. Further, the processor of the processing circuitry 302 may download programs from an external server via the communication interface 303.

Moreover, the processing circuitry 302 may be configured as hardware such as an ASIC (Application Specific Integrated Circuit) and an FPGA (Field Programmable Gate Array). Various functions of the ECG signal processing apparatus 1 can also be implemented by hardware processing with the use of an ASIC, an FPGA, or a special-purpose electronic circuit. Additionally or alternatively, the processing circuitry 302 may implement various functions of the ECG signal processing apparatus 1 by a combination of hardware and software processing.

Figure 4:
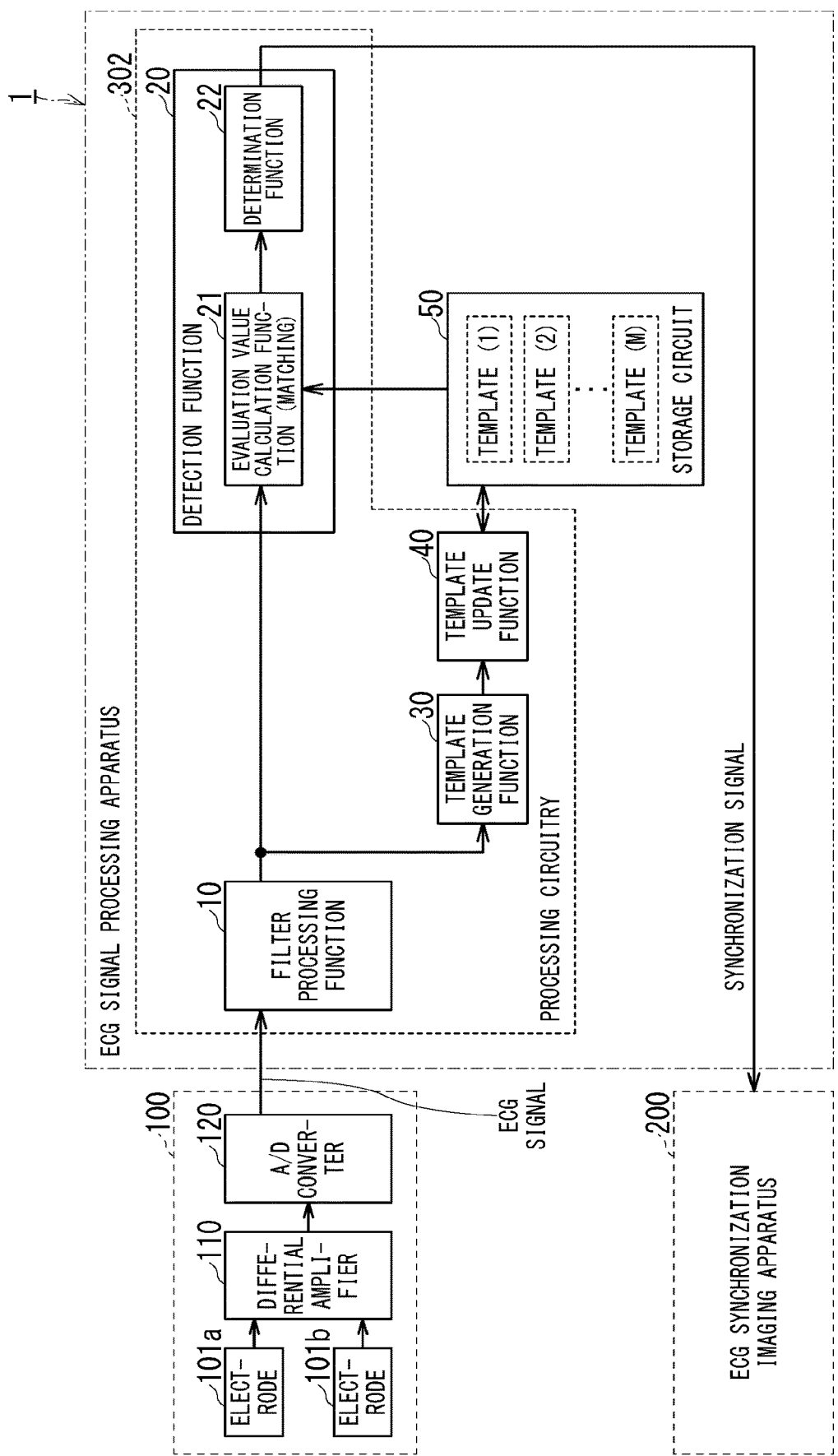
FIG. 4 is a functional block diagram showing an example of configuration of the ECG signal processing apparatus of the first embodiment and configuration of a device/apparatus connected to the ECG signal processing apparatus.

FIG. 4 is a block diagram showing an example of functional configuration of the ECG signal processing apparatus 1 of the first embodiment and configuration of a device/apparatus connected to the ECG signal processing apparatus 1. The electrocardiograph 100 generates ECG signals and transmits the ECG signals to the ECG signal processing apparatus 1. The ECG signal processing apparatus 1 generates synchronization signals from ECG signals, and transmits the generated synchronization signals to the ECG synchronization imaging apparatus 200.

The electrocardiograph 100 includes electrodes 101a and 101b, a differential amplifier 110, and an A/D (analogue to digital) converter 120. The electrodes 101a and 101b are set on a human body. The differential amplifier 110 amplifies a weak electrical potential difference between the electrodes 101a and 101b. The A/D converter 120 converts the analogue signal amplified by the differential amplifier 110 into a digital signal.

Although two electrodes 101a and 101b are illustrated, the number of electrodes of the electrocardiograph 100 is not limited to two. For example, in order to obtain a twelve-lead electrocardiogram, the electrocardiograph 100 may be configured to include four electrodes to be mounted on the respective four limbs and further six electrodes to be mounted on the chest part. In addition, instead of the method of obtaining an electrical potential difference between two points of a body, a method of recording an electrical potential difference between a predetermined reference and a mounting point of an electrode may be used.

The ECG signal processing apparatus 1 includes at least a storage circuit 50 and the above-described processing circuitry 302. The storage circuit 50 is a part of the memory circuit 307. The processing circuitry 302 implements a filter processing function 10, a detection function 20, a template generation function 30, and a template update function 40 by causing its processor to execute the programs being read out from the memory circuit 307.

The filter processing function 10 acquires an ECG signal from the electrocardiograph 100, and performs processing of enhancing an R-wave in the acquired ECG signal. The processing of enhancing an R-wave includes (a) processing of enhancing a high-frequency component of an ECG signal by using a high-pass filter configured to enhance a high-frequency component of an ECG signal and (b) processing of enhancing a specific frequency band of an ECG signal by using a band-pass filter. Hereinafter, an ECG signal subjected to the processing of enhancing a high-frequency component or the processing of enhancing a specific frequency band by the filter processing function 10 is referred to as an "enhanced ECG signal".

The template generation function 30 generates detection parameters for detecting an R-wave, from the enhanced ECG signal. As detection parameters for detecting an R-wave, various types are possible. A waveform template is one of detection parameters. In the present embodiment, a waveform template (hereinafter, simply referred to as a template) is generated by extracting a waveform near the R-wave from the entire waveform of the ECG signal time-sequentially inputted from the electrocardiograph 100.

The storage circuit 50 stores the generated template. Note that the storage circuit 50 stores two or more templates. As shown in FIG. 4 as an example, M templates from a template (1) to a template (M), which are different from each other, are stored in the storage circuit 50. Here, M is a natural number equal to or larger than two. The storage circuit 50 is configured as a rewritable memory.

The template update function 40 updates the templates stored in the storage circuit 50. As to a detailed method of updating, it will be described below.

The detection function 20 detects an R-wave from each of enhanced ECG signals time-sequentially outputted from the filter processing function 10, and generates a synchronization signal according to detection of each R-wave. Then, the detection function 20 outputs the generated synchronization signal to the ECG synchronization imaging apparatus 200.

The detection function 20 includes an evaluation value calculation function 21 and a determination function 22. The evaluation value calculation function 21 calculates an evaluation value based on the enhanced ECG signal and every one of the templates stored in the storage circuit 50. The determination function 22 detects an R-wave by comparing each of the calculated evaluation values with a predetermined threshold value.

As detection parameters for detecting an R-wave, feature quantity such as a peak value of an R-wave, a rising slope of an R-wave, a falling slope of an R-wave, and a half-value width of an R-wave may be used aside from templates. When an R-wave is detected by using the above-described feature quantity, the template generation function 30 generates detection parameters by extracting at least two parameters of the above-described feature quantity. In addition, the storage circuit 50 stores these detection parameters generated by the template generation function 30.

For example, when the detection parameter is a combination of a peak value and a half-value width of an R-wave, the storage circuit 50 stores plural combinations of a peak value and a half-value width of an R-wave. Further, in this case, the detection function 20 detects an R-wave by comparing detection parameters (i.e., a peak value and a half-value width of an R-wave) extracted from an enhanced ECG signal with the same detection parameters stored in the storage circuit 50, as matching processing. Although various types of feature quantity may be used for detection parameters as mentioned above, the following embodiments will be explained under the premise that each detection parameter is a template.

Figure 5:
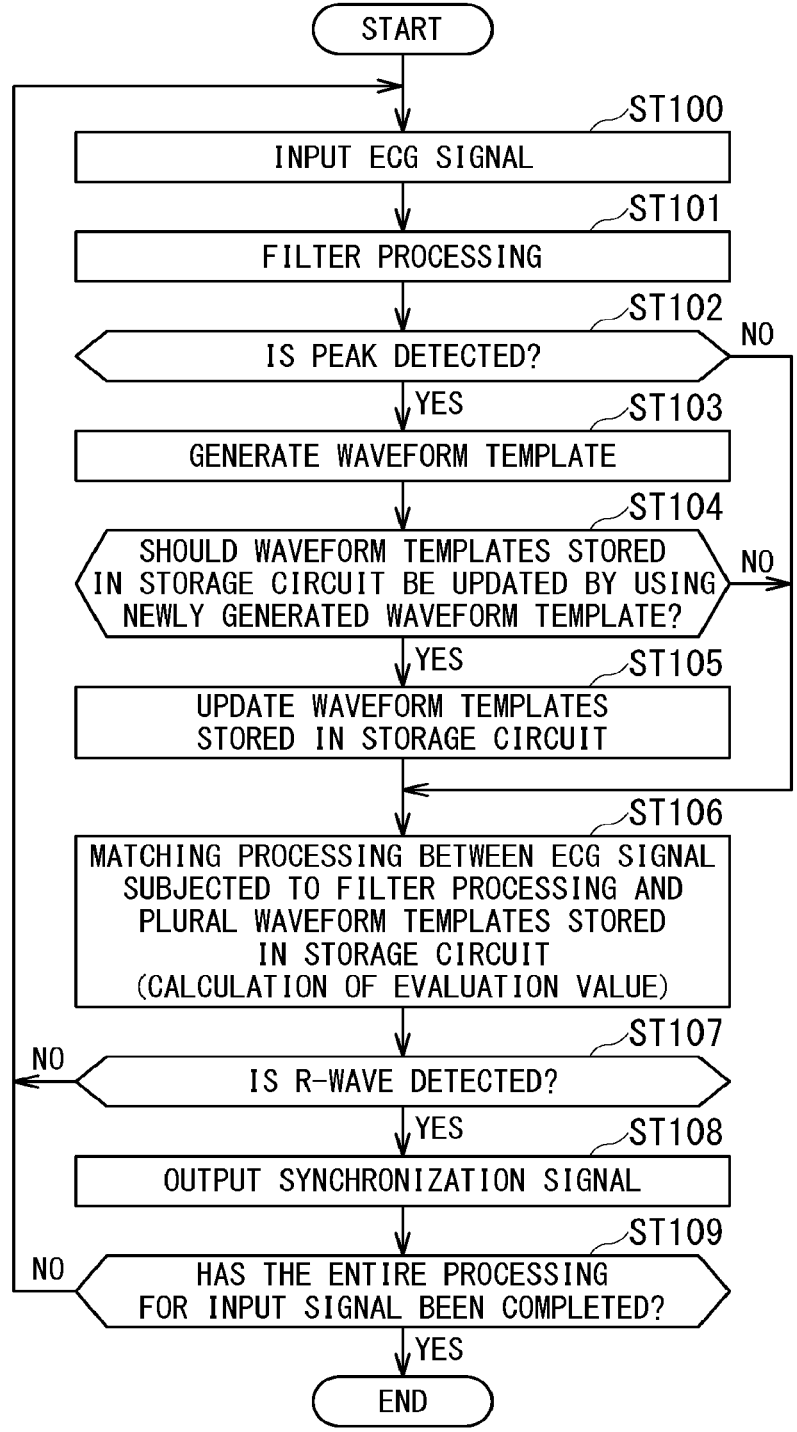
FIG. 5 is a flowchart showing an example of an operation performed by the ECG signal processing apparatus of the first embodiment.

FIG. 5 is a flowchart showing an example of an operation performed by the ECG signal processing apparatus 1 of the first embodiment.

The step ST100 and the step ST101 are processing corresponding to the filter processing function 10 of the processing circuitry 302. In the step ST100, an ECG signal is inputted to the processing circuitry 302 as one of time-sequential signals. The inputted ECG signal is a digital signal sampled by, for example, 1000 Hz in the A/D converter 120 of the electrocardiograph 100 (the sampling interval is one millisecond in the case of sampling by 1000 Hz). In order to reduce calculation burden after filter processing within the range which does not deteriorate performance such as a delay time, the filter processing function 10 may perform down-sampling of the ECG signal to the frequency of 500 Hz by thinning even-numbered or odd-numbered sampled data parts of the original ECG signal.

In the step ST101, the processing circuitry 302 generates an enhanced ECG signal by, for example, performing filter processing of enhancing a high-frequency component on the ECG signal subjected to the down-sampling processing.

Figure 6:
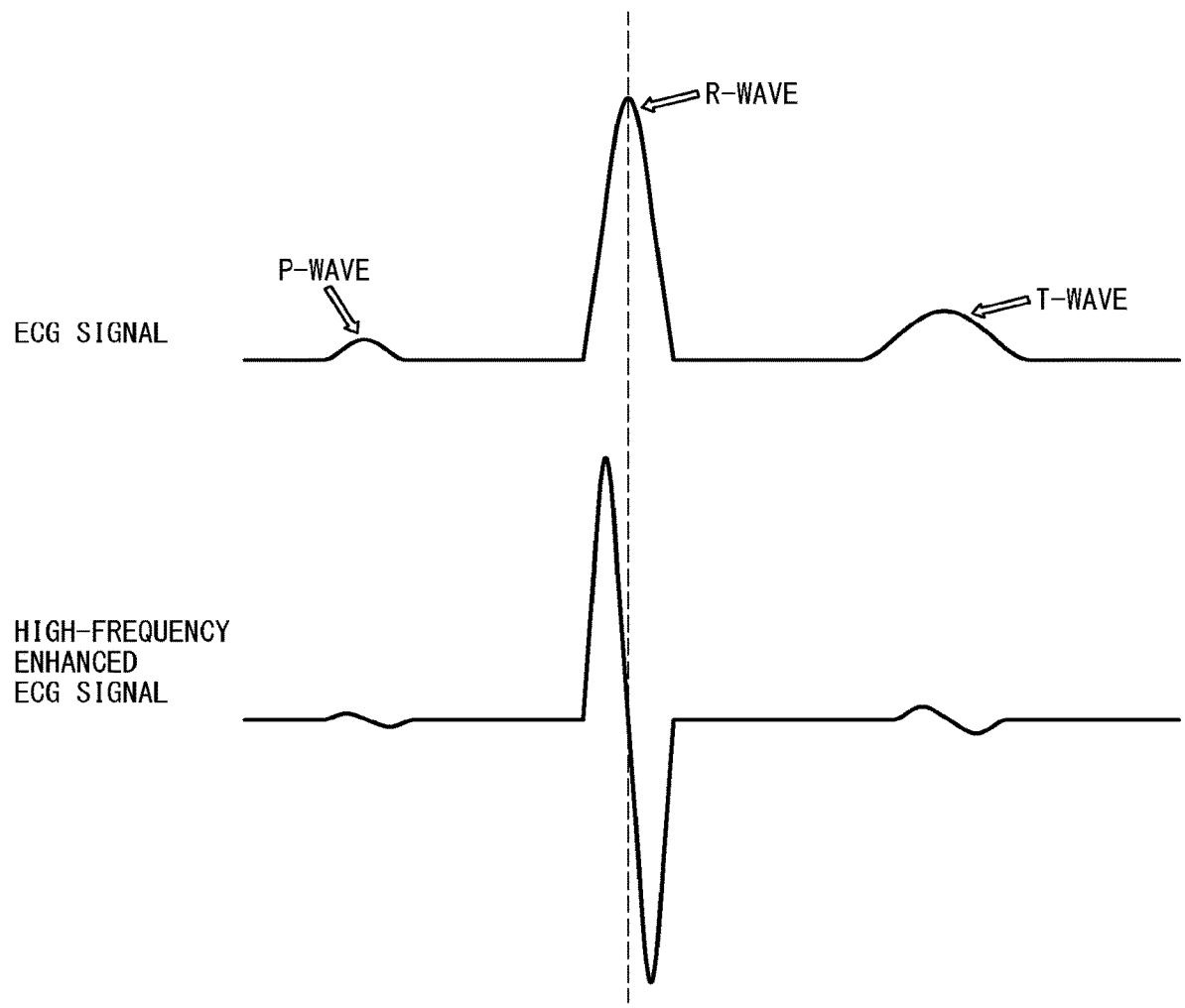
FIG. 6 is a schematic diagram showing a concept of a high-frequency enhanced ECG signal.

FIG. 6 is a schematic diagram showing a concept of an enhanced ECG signal. The upper part of FIG. 6 simplistically illustrates an example of a waveform of an inputted ECG signal, and the lower part of FIG. 6 simplistically illustrates an example of a waveform of the above ECG signal after being subjected to high-frequency enhancement processing. In the high-frequency enhancement processing, an R-wave having a steep rising slope and a steep falling slope is enhanced. By contrast, a T-wave and a P-wave are suppressed, since they have gentle rising and falling slopes. In order to reduce noise, a low-pass filter may be used in combination with a high-pass filter in the high-frequency enhancement processing.

Figure 7:
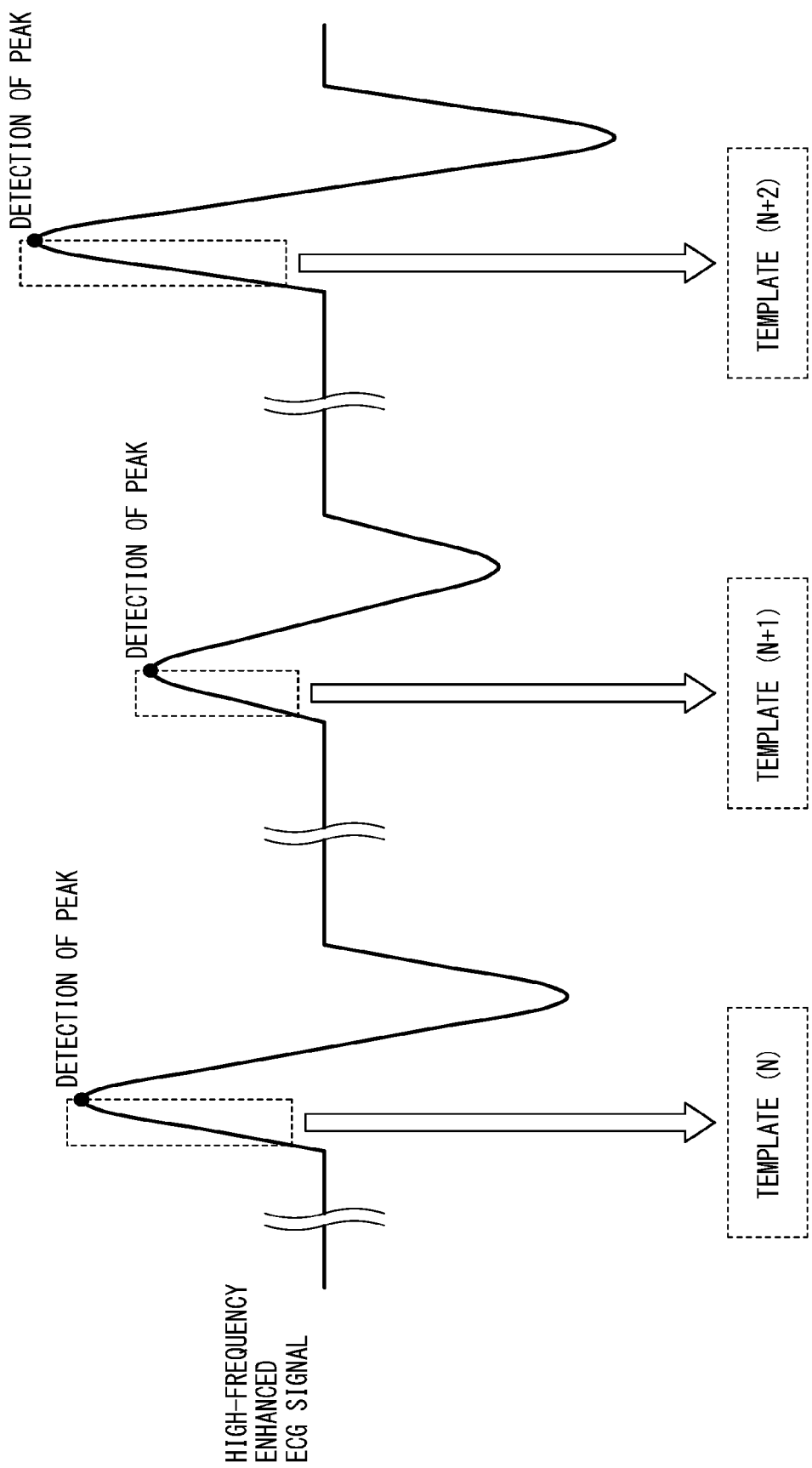
FIG. 7 is a schematic diagram showing a concept of template generation processing.

The steps ST102 and ST103 are processing corresponding to the template generation function 30 of the processing circuitry 302, and FIG. 7 shows the concept of generating templates by the template generation function 30.

In the step ST102, the processing circuitry 302 detects a peak of the enhanced ECG signal generated in the step ST101. When noise is small, a peak of an enhanced ECG signal approximately corresponds to the peak of its R-wave in general. The enhanced ECG signal is time-sequentially inputted to the template generation function 30 of the processing circuitry 302 at sampling intervals (e.g., at intervals of two millisecond), and processing of detecting a peak, i.e., determination as to whether a peak is arrived or not is performed at sampling intervals.

When a peak is detected (YES in the step ST102), the processing circuitry 302 generates a template by extracting a part of the R-wave based on the position of the detected peak from the inputted enhanced ECG signal.

FIG. 7 shows an example of generating a template (N), a template (N+1), and a template (N+2) by extracting a part of a waveform indicated by a broken line frame from the (N)th, (N+1)th, and (N+2)th R-waves, respectively, so that each of the extracted parts is temporally positioned immediately before the peak and has a predetermined time-length (i.e., W millisecond). As is clear from FIG. 7, when a peak height of each R-wave fluctuates between heartbeats, templates which are slightly different in shape from each other are generated.

The length of a past waveform to be extracted for generating a template is not limited to the above-described aspect (i.e., 10 milliseconds). For example, each template may be generated by extracting a part of a waveform from 20 milliseconds before the peak position to the peak position.

Note that detection of a peak of each enhanced ECG signal is processing for simply generating each template, and not processing for detecting each R-wave to generate a synchronization signal.

Next, the steps ST104 and ST105 are processing corresponding to the template update function 40 of the processing circuitry 302. In the step ST104, the processing circuitry 302 determines whether or not it updates templates stored in the storage circuit 50 by using newly generated templates, or determines a method of updating the templates. In the next step ST105, the processing circuitry 302 updates the templates stored in the storage circuit 50, in accordance with the determination in the step ST104.

Figure 8:
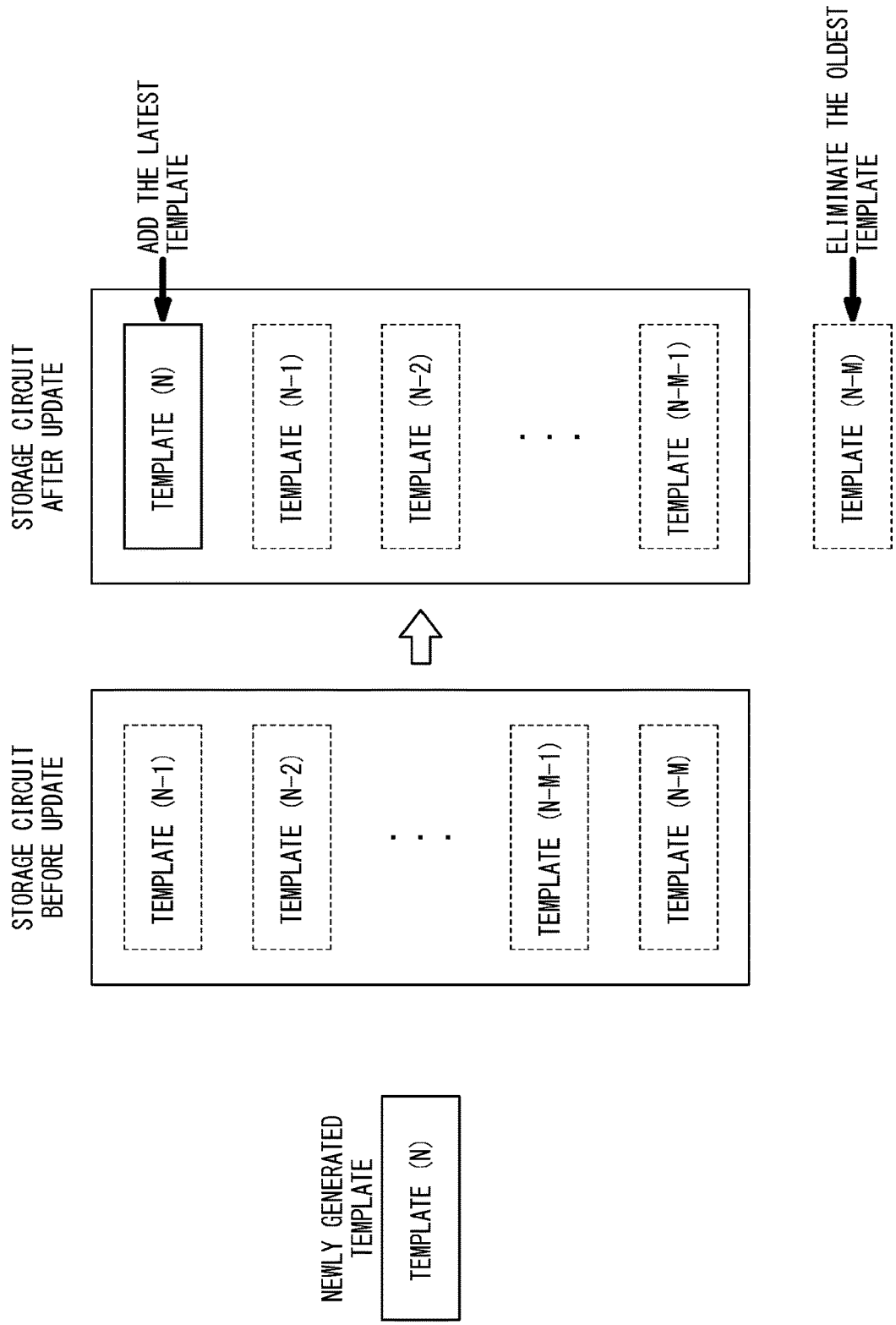
FIG. 8 is a schematic diagram showing a concept of template update processing.

As a method of updating, for example, the oldest template in the storage circuit 50 may be eliminated and the newly-generated latest template may be added to the templates to be stored in the storage circuit 50. For example, when M templates from the template (N-1) to the template (N-M) are stored in storage circuit 50 as shown in FIG. 8, the oldest template (N-M) is eliminated and the newly-generated latest template (N) is newly stored in the storage circuit 50. In this updating method, the templates in the storage circuit 50 are updated, each time a template is newly generated.

The steps ST106 to ST108 are processing corresponding to the detection function 20 of the processing circuitry 302. In the step ST106, the processing circuitry 302 performs matching processing between an enhanced ECG signal subjected to the filter processing and each of the templates stored in the storage circuit 50 so as to calculate an evaluation value for each of the templates, by its evaluation value calculation function 21.

Specifically, the processing circuitry 302 calculates a difference in intensity between the M-th template, which has length of W milliseconds and is stored in the storage circuit 50, and the latest part of the enhanced ECG signal whose length is also W milliseconds, for each sampling time used in the step ST100. Then, the processing circuitry 302 calculates the summation of the absolute values of the differences and defines the summation as an evaluation value $E_m$. Since this evaluation value $E_m$ is calculated for each of the templates stored in the storage circuit 50, M evaluation values $E_m$ are calculated when the total number of the templates stored in the memory circuits 50 is M.

In the step ST107, the processing circuitry 302 calculates the minimum value Emin of the M evaluation values $E_m$, and detects an R-wave by performing threshold processing on the minimum value Emin, as its determination function 22. Specifically, when the minimum value Emin is smaller than a predetermined threshold value, the processing circuitry 302 determines that an R-wave is detected.

When an R-wave is detected, the processing circuitry 302 generates a synchronization signal and outputs the generated synchronization signal to the ECG synchronization imaging apparatus 200 in the step ST108. When an R-wave is not detected, the processing returns to the step ST100.

Although a difference between an enhanced ECG signal and each of the templates is used for an evaluation value in the above processing, a correlation value between an enhanced ECG signal and each of the templates may be used for an evaluation value instead of the above-described difference. In this case, the determination function 22 of the processing circuitry 302 calculates the maximum value Emax of the M evaluation values $E_m$ and determines that an R-wave is detected when the maximum value Emax is larger than a predetermined threshold value.

The step ST109 is determination processing as to whether the entire processing should be completed or not, and the processing circuitry 302 repeats the processing of the steps ST100 to ST108 until a command to complete the processing is inputted from outside.

The above-described ECG signal processing apparatus 1 of the first embodiment is configured to store plural templates, which are different from each other, in the storage circuit 50. Therefore, even if a waveform of an R-wave included in each of enhanced ECG signals (e.g., a wave height value of each R-wave) inputted to the detection function 20 fluctuates for each R-wave, the fluctuated R-wave can be detected with high reliability in the case where the fluctuated R-wave is similar to one of the plural templates stored in the storage circuit 50. In other words, robustness of detection to fluctuating ECG signals can be improved by detecting an R-wave with the use of plural templates.

Figure 9:
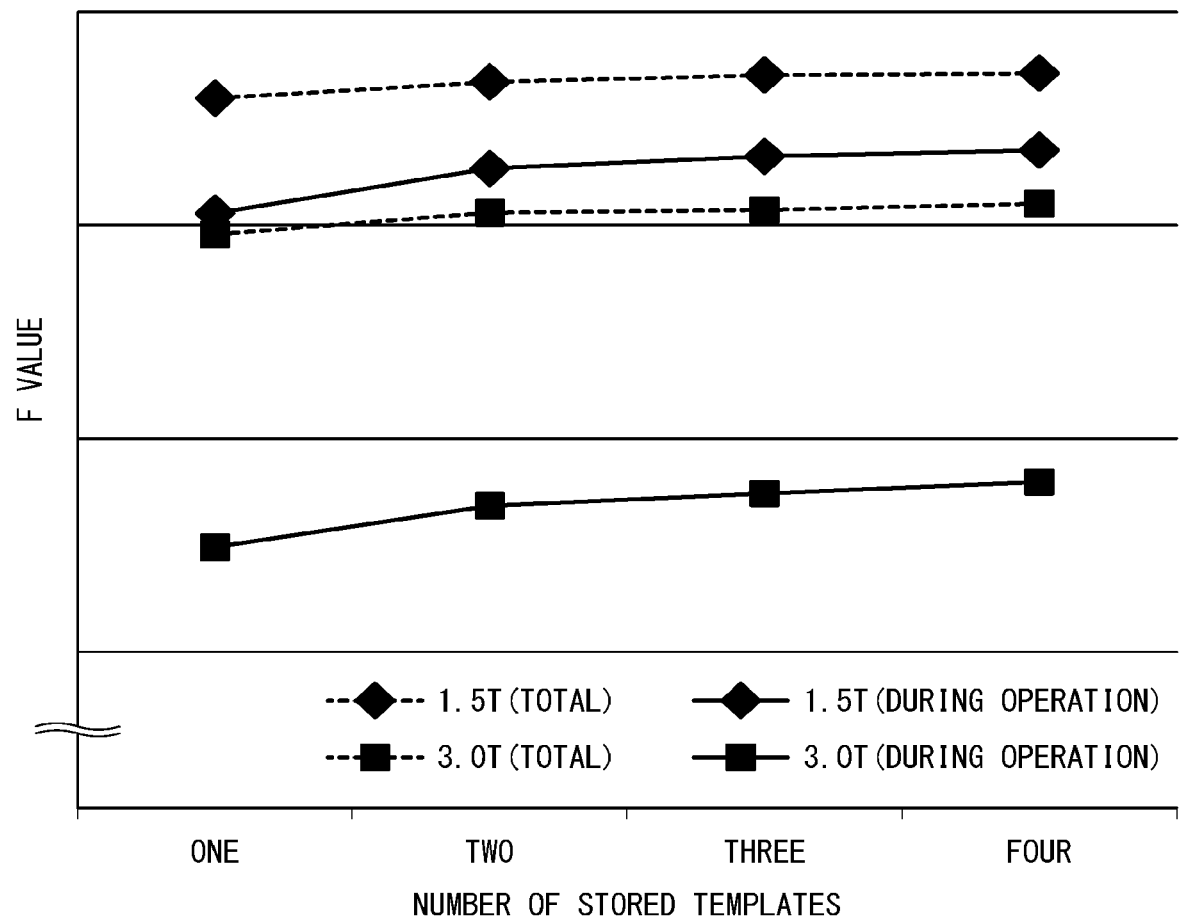
FIG. 9 is a schematic chart showing results of performing detection of R-waves on ECG signals, for confirming the effect of the ECG signal processing apparatus of the first embodiment.

FIG. 9 is a schematic chart showing results of performing detection of R-waves on ECG signals, for confirming the effect of the ECG signal processing apparatus 1 of the first embodiment. Thirteen volunteers underwent MRI diagnosis with the use of an MRI apparatus of 1.5 Tesla and another MRI apparatus of 3.0 Tesla, and an evaluation is made on how many of the total number of R-waves included in ECG signals acquired during the MRI diagnosis can be accurately detected. Out of the total R-waves (22298, in this example), 8006 R-waves were acquired in an operating state of the MRI apparatus (i.e., during imaging), and the rest of the R-waves were acquired in a non-operating state of the MRI apparatus. An F value is used for an evaluation index and the vertical axis of the chart in FIG. 9 indicates F values. An F value can be calculated from the following formulas (1) to (3).

$$F \text{ value} = (2*PR)/(P+R): \qquad \text{Formula (1)}$$

$$P = TP/(TP+FP): \qquad \text{Formula (2)}$$

$$R = TP/(TP+FN): \qquad \text{Formula (3)}$$

In the above test, a case where an R-wave is detected with an error within the range of ±20 milliseconds from the correct R-wave position is treated as success. In addition, TP (True Positive) indicates the number of success, FP (False Positive) indicates the number of erroneous detection (i.e., an R-wave is incorrectly detected), and FN indicates the number of missing (i.e., failure in detecting an R-wave which should have been detected). An F value is an evaluation index in which the above-described erroneous detection and missing are reflected in addition to success. The higher an F value is, the higher reliability of detection becomes.

The horizontal axis of the chart in FIG. 9 indicates the number of templates stored in the storage circuit 50. Especially in an operating state of the MRI apparatus (i.e., during imaging), an F value is improved by increasing the number of templates, and the above-described effect of the processing performed by the ECG signal processing apparatus 1 can be confirmed.

(Modification of First Embodiment)

In the above-described first embodiment, the oldest template of all the templates stored in the storage circuit 50 is eliminated and a newly generated template is added in the processing of updating templates in the steps ST104 and ST105 in FIG. 5 (see also FIG. 8). On the other hand, in the modification of the first embodiment, a similarity value between the newly generated template and each of the templates stored in the storage circuit 50 is calculated, and the templates in the storage circuit 50 is updated by storing the newly generated template when this similarity value is determined to be smaller than a predetermined value.

Figure 10:
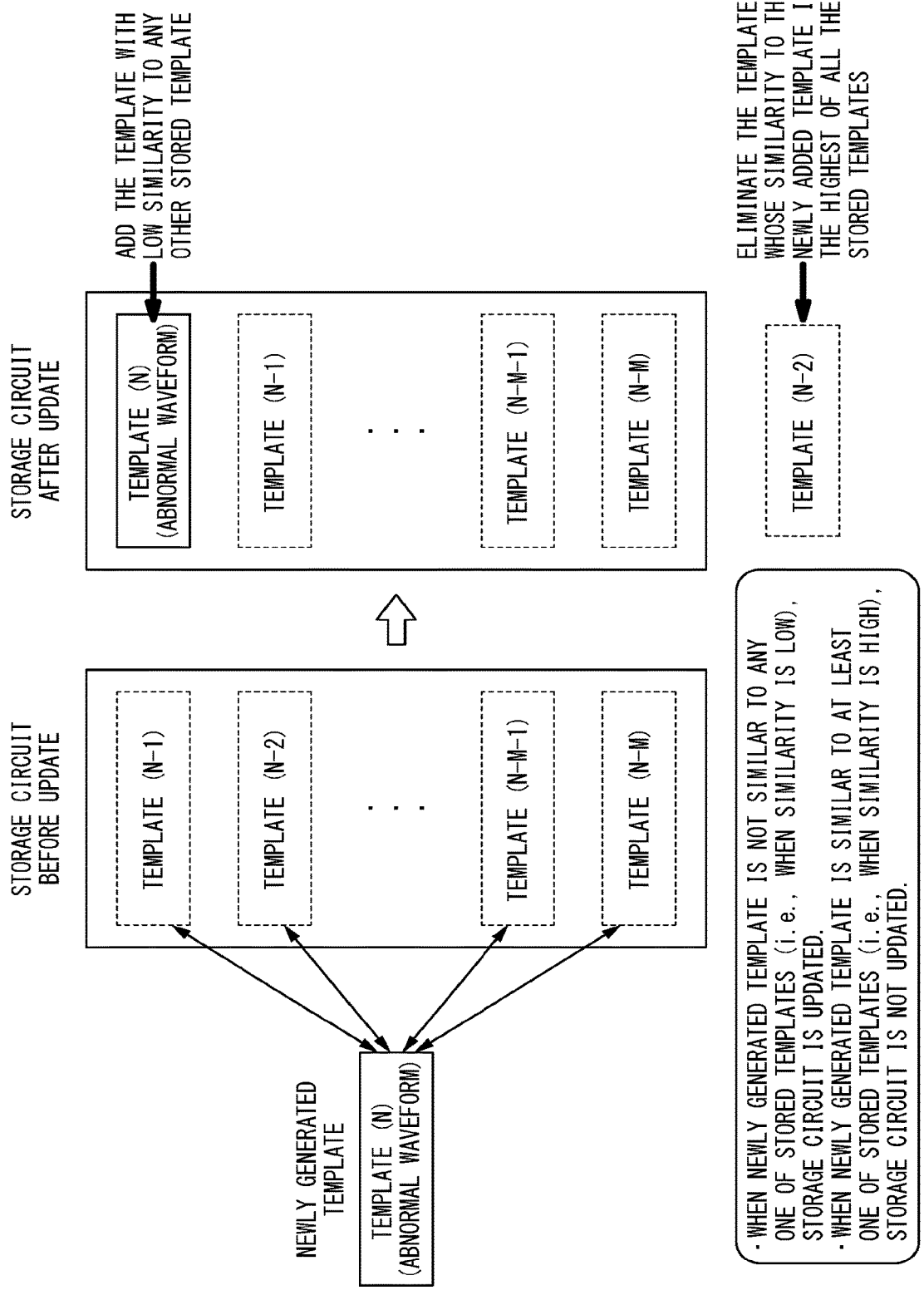
FIG. 10 is a schematic diagram showing a concept of updating templates in a modification of the first embodiment.

Specifically, as shown in FIG. 10, the ECG signal processing apparatus 1 is configured to update the templates stored in the storage circuit 50, when the newly generated template is not similar to any one of the templates stored in the storage circuit 50 (i.e., when the similarity value is low). By contrast, when the newly generated template is similar to at least one of the templates stored in the storage circuit 50 (i.e., when the similarity value is high), the ECG signal processing apparatus 1 does not update the templates stored in the storage circuit 50.

In this modification, the newly generated template having a low similarity value is stored in the storage circuit 50 as one of the templates to be used for detection and the template having the highest similarity value to the newly generated template of all the templates stored in the storage circuit 50 at this update timing is eliminated.

Only the templates, which have low similarity to each other, remain in the storage circuit 50 by such an update method. As a result, when an abnormal waveform is included in ECG signals as shown in FIG. 12A to be described below, the template generated based on this abnormal waveform is stored in the storage circuit 50 as an abnormal waveform template and remains in the storage circuit 50 after the storage. Therefore, when an abnormal waveform similar to the above-described abnormal waveform template arrives next time, this abnormal waveform can be detected by using the abnormal waveform template which has been already stored.

Second Embodiment

Figure 11:
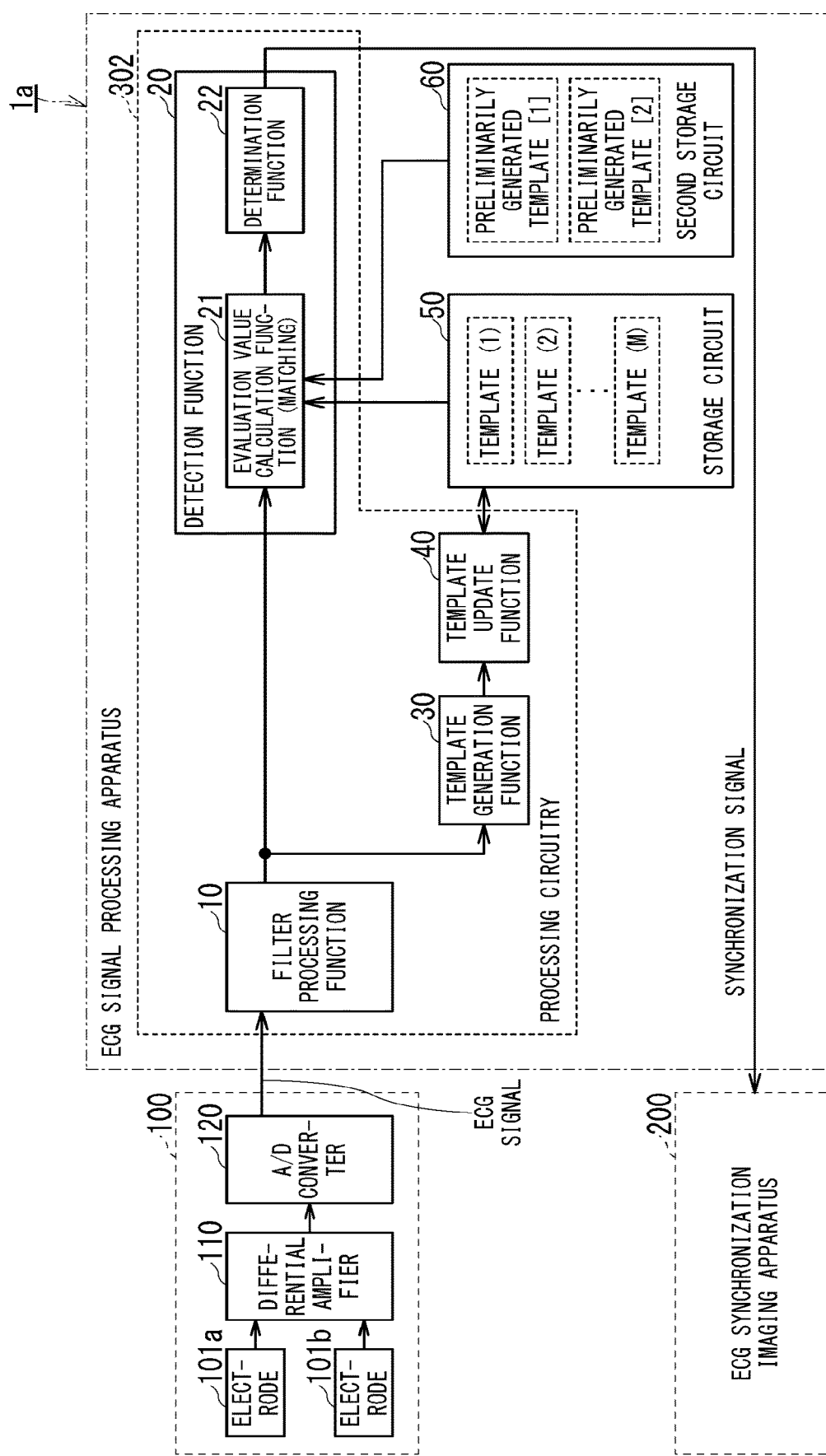
FIG. 11 is a functional block diagram showing an example of configuration of the ECG signal processing apparatus of the second embodiment.

FIG. 11 is a functional block diagram showing an example of configuration of the ECG signal processing apparatus 1a of the second embodiment. The ECG signal processing apparatus 1a of the second embodiment has configuration in which a second storage circuit 60 is added to the configuration of the ECG signal processing apparatus 1 of the first embodiment.

The second storage circuit 60 stores at least one preliminarily generated fixed template. Preferably, the second storage circuit 60 stores two or more preliminarily generated fixed templates. The above-described "preliminarily generated" means to generate the fixed template(s) before an object undergoes diagnosis using the ECG synchronization imaging apparatus 200. Each preliminarily generated template may be generated from an enhanced ECG signal obtained by performing filter processing on an ECG signal of the same object, or may be generated from an enhanced ECG signal of a different object. In addition, a representative template may be generated by averaging templates which are generated from different objects, as the preliminarily generated template.

Although the second storage circuit 60 stores at least one preliminarily generated template based on a normal waveform of an ECG signal, it is preferable that the second storage circuit 60 stores plural types of preliminarily generated templates including a template corresponding to a normal waveform and a template corresponding to an abnormal waveform.

The processing performed by the ECG signal processing apparatus 1a of the second embodiment is basically the same as that of the first embodiment. However, the processing of calculating an evaluation value in the step ST106 and the processing of determining whether an R-wave is detected or not in the step ST107 in the flowchart of FIG. 5 are slightly different between the first and second embodiments.

In the step ST106 of the second embodiment, an evaluation value is calculated for each of the templates stored in the storage circuit 50 and the preliminarily generated templates stored in the second storage circuit 60. In other words, when the number of templates to be stored in the storage circuit 50 is defined as M and the number of preliminarily generated templates to be stored in second storage circuit 60 is defined as K, the evaluation value calculation function 21 calculates M+K evaluation values. In the next step ST107 of the second embodiment, the current processing target waveform is detected as an R-wave, when the minimum value Emin of those M+K evaluation values is smaller than the predetermined threshold value.

FIG. 12A to FIG. 12E are timing charts for explaining the effect of the ECG signal processing apparatus 1a of the second embodiment in comparison with conventional detection methods. Especially, a case where abnormal waveforms are included in ECG signals as shown in FIG. 12A is compared between the second embodiment and a conventional detection method. Conventionally, a method of detecting an R-wave by using one preliminarily generated fixed template (hereinafter, referred to as a conventional method (1)), or another method of detecting an R-wave by using only one template which is sequentially updated (hereinafter, referred to as a conventional method (2)) have been used.

The conventional method (1) fails in detection of abnormal waveforms as shown in FIG. 12B, when the fixed template is generated based on a normal waveform. Further, the conventional method (1) fails in detection of normal waveforms as shown in FIG. 12C, when the fixed template is generated based on an abnormal waveform.

The conventional method (2) continues to fail in detection from start of acquiring ECG signals until a template to be sequentially updated is generated, as shown in FIG. 12D. In addition, the number of templates to be sequentially updated is only one. Thus, when an abnormal waveform arrives after the template is updated to become a template based on a normal waveform, the conventional method (2) cannot detect this abnormal waveform.

By contrast, the ECG signal processing apparatus 1a of the second embodiment includes the second storage circuit 60 configured to store at least one fixed template in addition to the storage circuit 50 configured to store plural templates to be sequentially updated. Further, the second storage circuit 60 stores a template [1] corresponding to a normal waveform and a template [2] corresponding to an abnormal waveform, as its desirable aspect. Such configuration of the second embodiment enables detection of both of abnormal waveforms and normal waveforms by using the template [1] and the template [2] preliminarily stored in the second storage circuit 60, even immediately after the start of acquiring ECG signals as shown in FIG. 12E.

In addition, the ECG signal processing apparatus 1a of the second embodiment can robustly detect R-waves by using plural templates to be sequentially updated, after templates are generated and stored in the storage circuit 50. Furthermore, since at least one template corresponding to a normal waveform and at least one template corresponding to an abnormal waveform are generated based on the waveform of the latest ECG signal and stored in the storage circuit 50 as explained in the modification of the first embodiment, both of abnormal waveforms and normal waveforms can be robustly detected.

Third Embodiment

Figure 13:
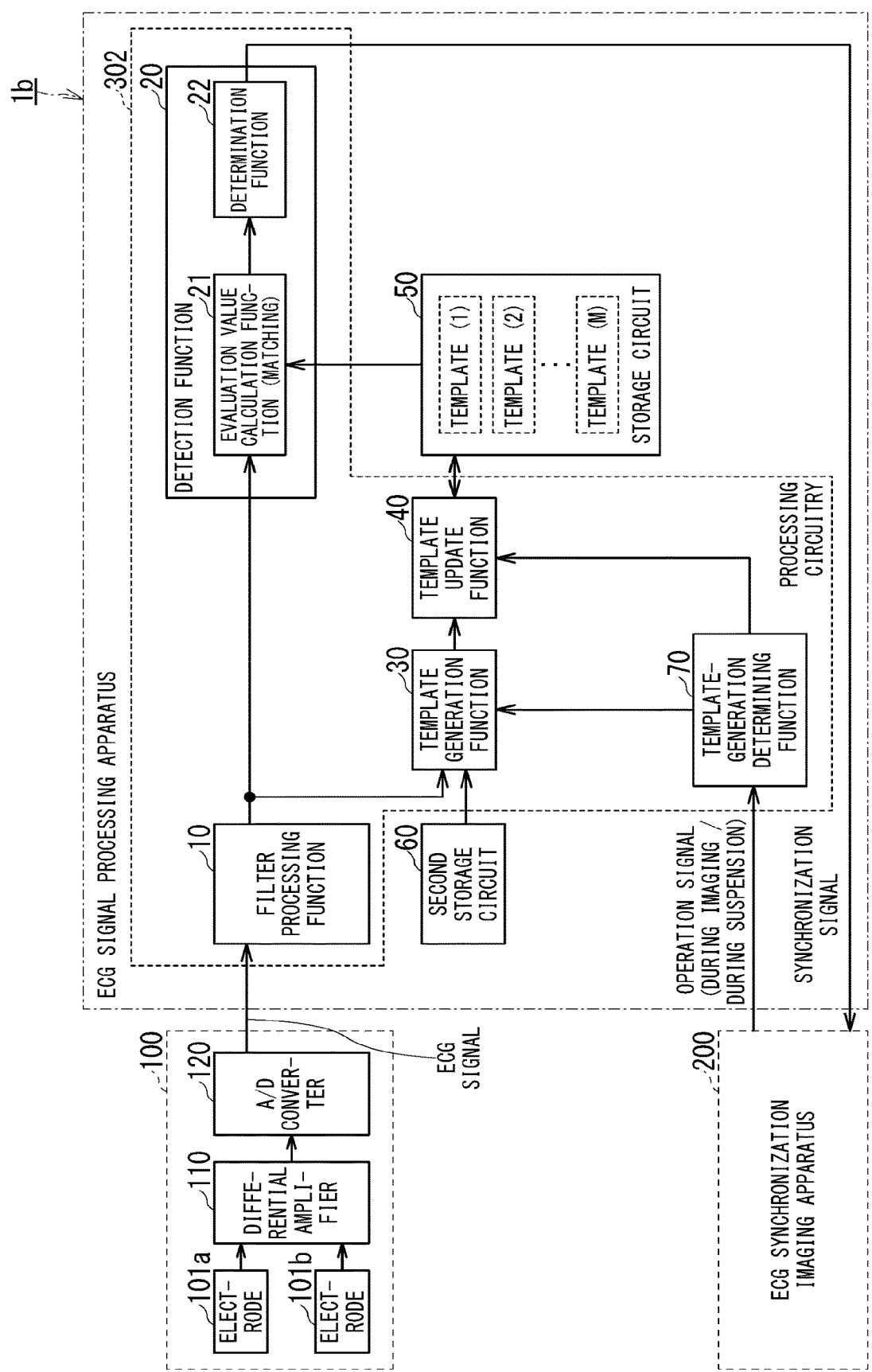
FIG. 13 is a functional block diagram showing an example of configuration of the ECG signal processing apparatus of the third embodiment.

FIG. 13 is a functional block diagram showing an example of configuration of the ECG signal processing apparatus 1b of the third embodiment. In the configuration of the ECG signal processing apparatus 1b of the third embodiment, a template-generation determining function 70 is added to that of the second embodiment. The template-generation determining function 70 is also a function implemented by the processing circuitry 302.

Figure 14:
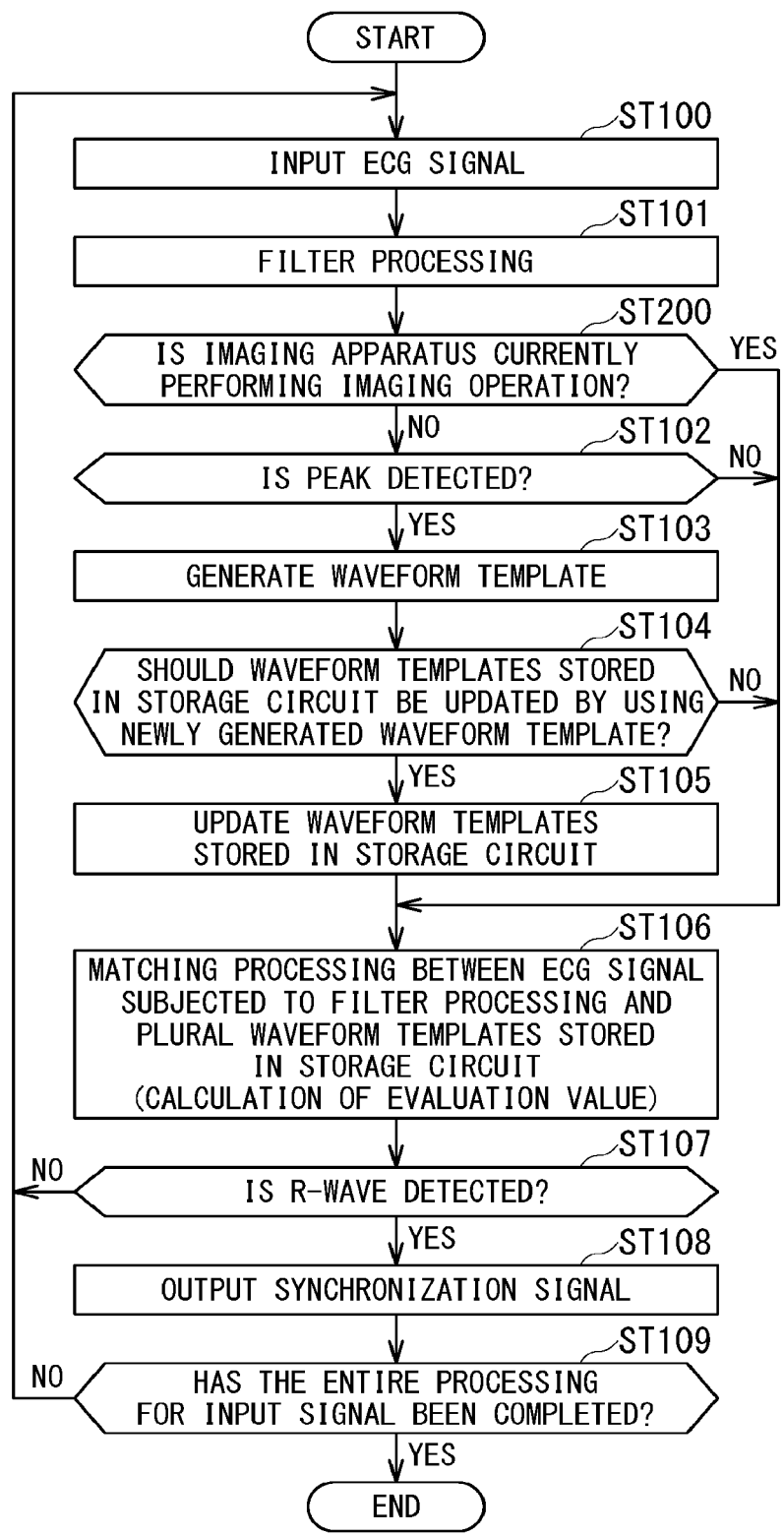
FIG. 14 is a flowchart showing an example of an operation performed by the ECG signal processing apparatus of the third embodiment.

FIG. 14 is a flowchart showing an example of an operation performed by the ECG signal processing apparatus 1b of the third embodiment. The processing of the step ST200 is added to the flowchart of the first and second embodiments shown in FIG. 5.

In the step ST200, the processing circuitry 302 monitors an operating state of the ECG synchronization imaging apparatus 200 by its template-generation determining function 70, and determines whether it generates a new template by its template generation function 30 or not, depending on the operating state of the ECG synchronization imaging apparatus 200.

For example, when the ECG synchronization imaging apparatus 200 is an MRI apparatus, the processing circuitry 302 acquires an operation signal indicative of the current state of the MRI apparatus as to whether it is during imaging or it is in a non-operating state (i.e., imaging is not performed). Thereby, the processing circuitry 302 determines whether the MRI apparatus is currently performing imaging or not. When imaging is currently performed, the processing circuitry 302 skips the processing of the steps ST102 and ST103, i.e., the processing circuitry 302 does not perform processing of generating a new template from an enhanced ECG signal. In addition, when imaging is currently performed, the processing circuitry 302 also skips the processing of the steps ST104 and ST105 and does not perform processing of updating templates stored in the storage circuit 50.

FIG. 15A to FIG. 15E are timing charts showing examples of operations performed by the ECG signal processing apparatus 1b of the third embodiment. As shown in FIG. 15A and FIG. 15B (see also FIG. 2A to FIG. 2C), when an MRI apparatus is in a non-operating state, noise superimposed on ECG signals is small. However, in a period during which imaging is performed by an MRI apparatus, large noise is superimposed on ECG signals due to influence of gradient magnetic fields and RF magnetic fields generated by the MRI apparatus. If a template is generated from an ECG signal on which such large noise is superimposed, a template whose waveform is greatly different from the waveform to be detected (i.e., an R-wave) is generated and accurate detection cannot be expected.

For the above reason, as shown in FIG. 15C and FIG. 15D, generation and update of templates are stopped during imaging in the third embodiment. Instead, templates which were stored in the storage circuit 50 at the timing immediately before start of imaging are held during this imaging, and R-waves are detected by using these templates held in the storage circuit 50 during this imaging. Although considerably large noise is superimposed on ECG signals as detection targets, templates used for matching processing are not influenced by noise and thus R-waves can be detected with high reliability.

In an MRI apparatus, plural protocols (e.g., plural imaging sequences for acquiring plural types of images such as T1 weighted images and T2 weighted images) are sometimes performed in series based on imaging conditions inputted by an operator. In such a case, a non-operating period, which has length of a certain degree, may exist between completion of a certain protocol and start of the next protocol. In this case, generation and update of templates can be resumed during the non-operating period.

In FIG. 13, the template generation function 30 of the processing circuitry 302 determines the timing to extract a part of a waveform from an enhanced ECG signal for generating a template, by performing matching processing between the enhanced ECG signal and each of the preliminarily generated templates stored in the second storage circuit 60. Specifically, when an R-wave is detected by performing matching processing between the enhanced ECG signal and each of the preliminarily generated templates, a new template is generated by extracting a part of the waveform of the enhanced ECG signal which starts W milliseconds, e.g., 20 milliseconds before this detection position of this R-wave and ends at this detection position. Also in the third embodiment, the template generation function 30 may independently detect each peak of enhanced ECG signals and determine each timing to extract a new template in a manner similar to the first embodiment.

Fourth Embodiment

Figure 16:
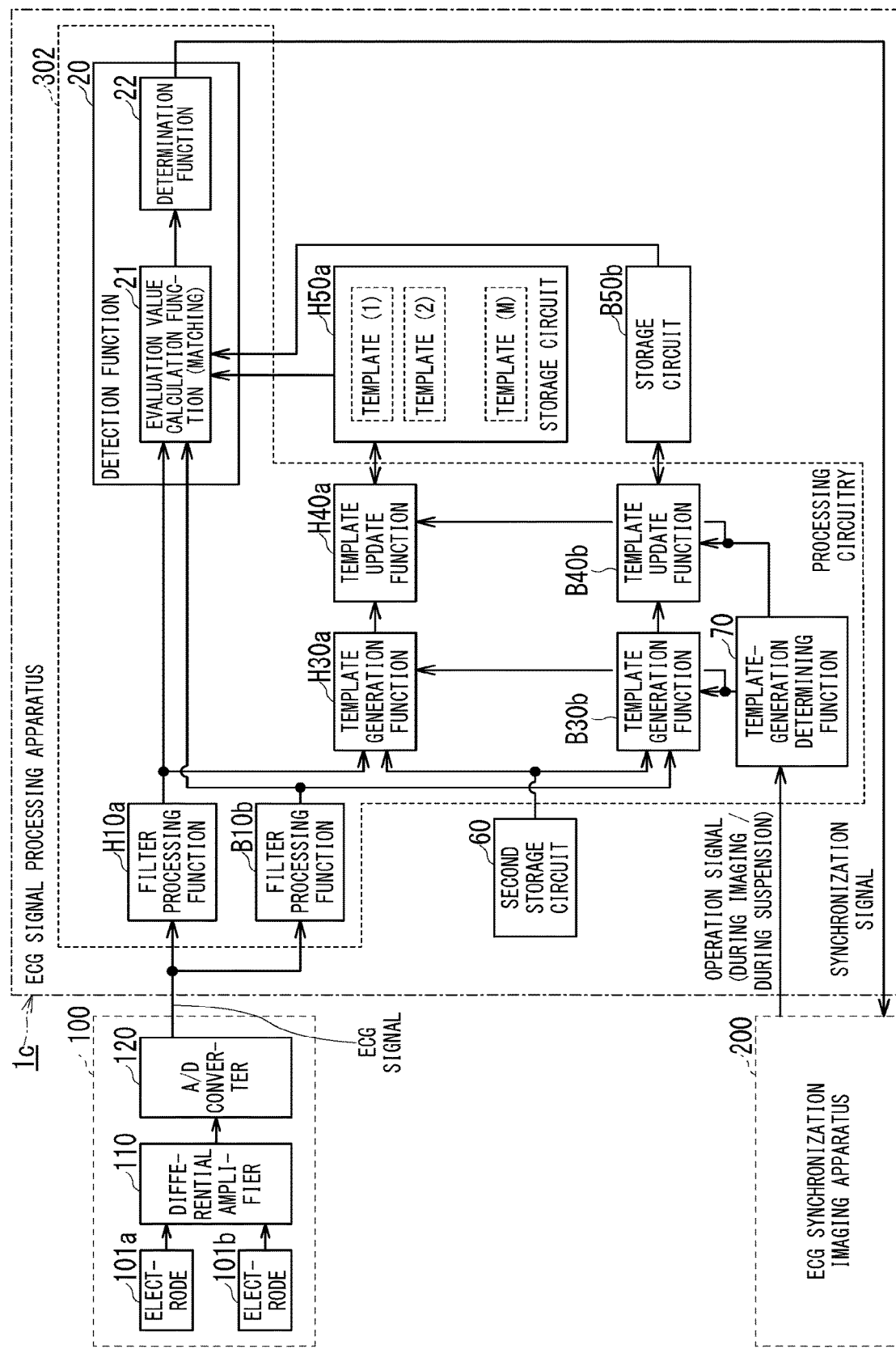
FIG. 16 is a functional block diagram showing an example of configuration of the ECG signal processing apparatus of the fourth embodiment.

FIG. 16 is a functional block diagram showing an example of configuration of the ECG signal processing apparatus 1c of the fourth embodiment. Although configuration of the third embodiment has the filter processing function 10 equipped with either a high-pass filter or a band-pass filter, configuration of the fourth embodiment includes both a filter processing function H10a equipped with a high-pass filter and a filter processing function B10b equipped with a band-pass filter.

High-frequency enhanced ECG signals are outputted from the filter processing function H10a, and band-enhanced ECG signals are outputted from the filter processing function Blob. In accordance with these two filter processing functions H10a and Blob, the ECG signal processing apparatus 1c includes two template generation functions H30a and B30b, two template update functions H40a and B40b, and two storage circuits H50a and B50b.

High-frequency enhanced ECG signals are subjected to processing in the template generation function H30a and the template update function H40a, and the generated and/or updated template is stored in the storage circuit H50a. Meanwhile, band-enhanced ECG signals are subjected to processing in the template generation function B30b and the template update function B40b, and the generated and/or updated template is stored in the storage circuit B50b.

Further, both of the high-frequency enhanced ECG signals and the band-enhanced ECG signals are inputted to the detection function 20.

The evaluation value calculation function 21 of the detection function 20 calculates M evaluation values of a high-frequency enhanced ECG signal compared with the respective M templates stored in the storage circuit H50a. In other words, the summation of absolute values of differences in intensity of respective parts of the entire waveform divided based on sampling time between one template and a high-frequency enhanced ECG signal is calculated as the evaluation value for each of M templates. Then, the evaluation value calculation function 21 defines the minimum value of M evaluation values as a high-frequency enhanced evaluation value EHmin.

Similarly, the evaluation value calculation function 21 calculates M evaluation values of a band-enhanced ECG signal compared with the respective M templates stored in the storage circuit B50b (as the summation of absolute values of differences in intensity of respective parts of the entire waveform between both), and defines the minimum value of these M evaluation values as a band-enhanced evaluation value EBmin.

Furthermore, the evaluation value calculation function 21 calculates the weighted average of the high-frequency enhanced evaluation value EHmin and the band-enhanced evaluation value EBmin as a combined evaluation value E. Specifically, when weighting coefficients are defined as α and (1−α) on the premise that α is within the range of zero to 1, the combined evaluation value E is calculated by the formula as follows.

$$E = \alpha * EH\text{min} + (1-\alpha) * EB\text{min}$$

The determination function 22 detects an R-wave by using the calculated combined evaluation value E. Specifically, when the combined evaluation value E is smaller than a predetermined threshold value, the detected target is determined to be an R-wave.

Incidentally, the determination function 22 may always determine that the detected target is not an R-wave for a predetermined period after detection of an R-wave. In addition, when ECG signals of plural channels are outputted from the electrocardiograph 100, the determination function 22 may calculate the complex evaluation values E for the respective channels and determine whether the detected target is an R-wave or not, by comparing the predetermined threshold value with the average of the complex evaluation values E.

Figure 17A:
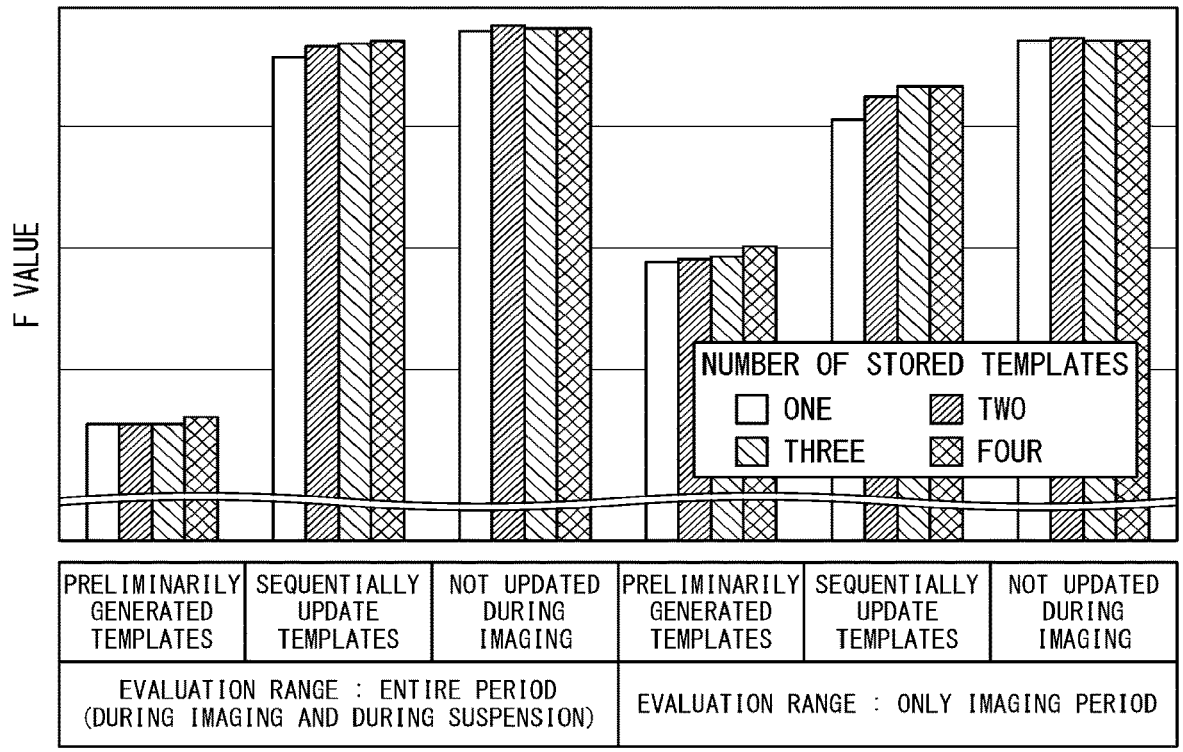
FIG. 17A and FIG. 17B are diagrams showing results of evaluation test for confirming the effect of the ECG signal processing apparatus of the fourth embodiment.
Figure 17B:
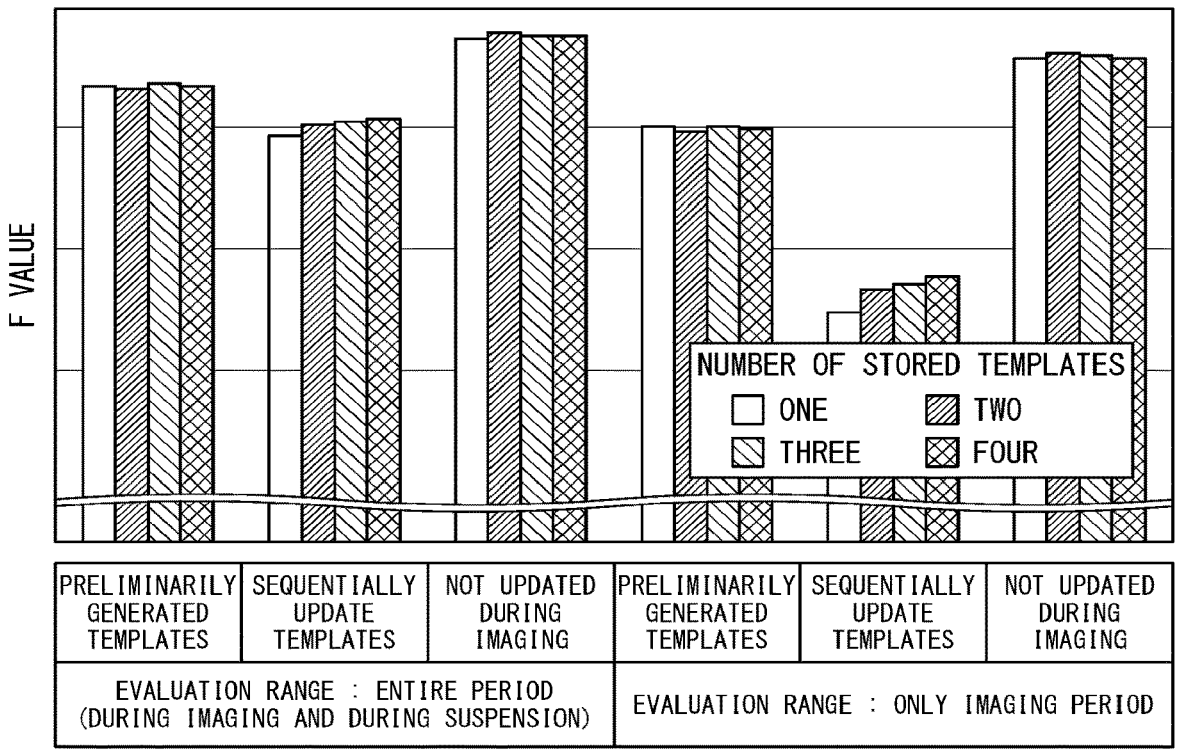

FIG. 17A and FIG. 17B are diagrams showing results of evaluation test performed for confirming the effect of the ECG signal processing apparatus 1c of the fourth embodiment. FIG. 17A shows a detection result of R-waves by using an MRI apparatus of 1.5 Tesla, and FIG. 17B shows a detection result of R-waves by using an MRI apparatus of 3.0 Tesla.

Data of ECG signals used for the above evaluation are the same as those of FIG. 9, an evaluation is made on how many of the total number of R-waves included in acquired ECG signals can be accurately detected. Out of the total R-waves (22298, in this example), 8006 R-waves were acquired in an operating state of the MRI apparatus (i.e., during imaging), and the rest of the R-waves were acquired in a non-operating state of the MRI apparatus. An F value is used for an evaluation index in a manner similar to FIG. 9 and the vertical axis of each of FIG. 17A and FIG. 17B indicates F values.

In the horizontal axis of each of FIG. 17A and FIG. 17B, "evaluation range: entire period (during imaging and during suspension)" means the total R-waves (22298) are evaluation targets, and "evaluation range: only imaging period" means 8006 R-waves acquired during imaging are evaluation targets.

The vertical bar chart corresponding to "preliminarily generated templates" in the horizontal axis of each of FIG. 17A and FIG. 17B shows an evaluation result of detecting R-waves by using fixed templates which have been preliminarily generated. In addition, the vertical bar chart corresponding to "sequentially update templates" in the horizontal axis of each of FIG. 17A and FIG. 17B shows an evaluation result of detecting R-waves by sequentially updating templates during imaging and during suspension. Further, the vertical bar chart corresponding to "not updated during imaging" in the horizontal axis of each of FIG. 17A and FIG. 17B shows an evaluation result of detecting R-waves by using the ECG signal processing apparatus 1c of the fourth embodiment, i.e., templates are not updated during imaging but updated only during suspension.

According to FIG. 17A and FIG. 17B, it can be recognized that the ECG signal processing apparatus 1c of the fourth embodiment has high detection performance. Especially, in the MRI apparatus of 3.0 Tesla, it is shown that performance of "not updated during imaging" corresponding to the fourth embodiment is more improved compared with the performance of "preliminarily generated templates" and "sequentially update templates".

Figure 18:
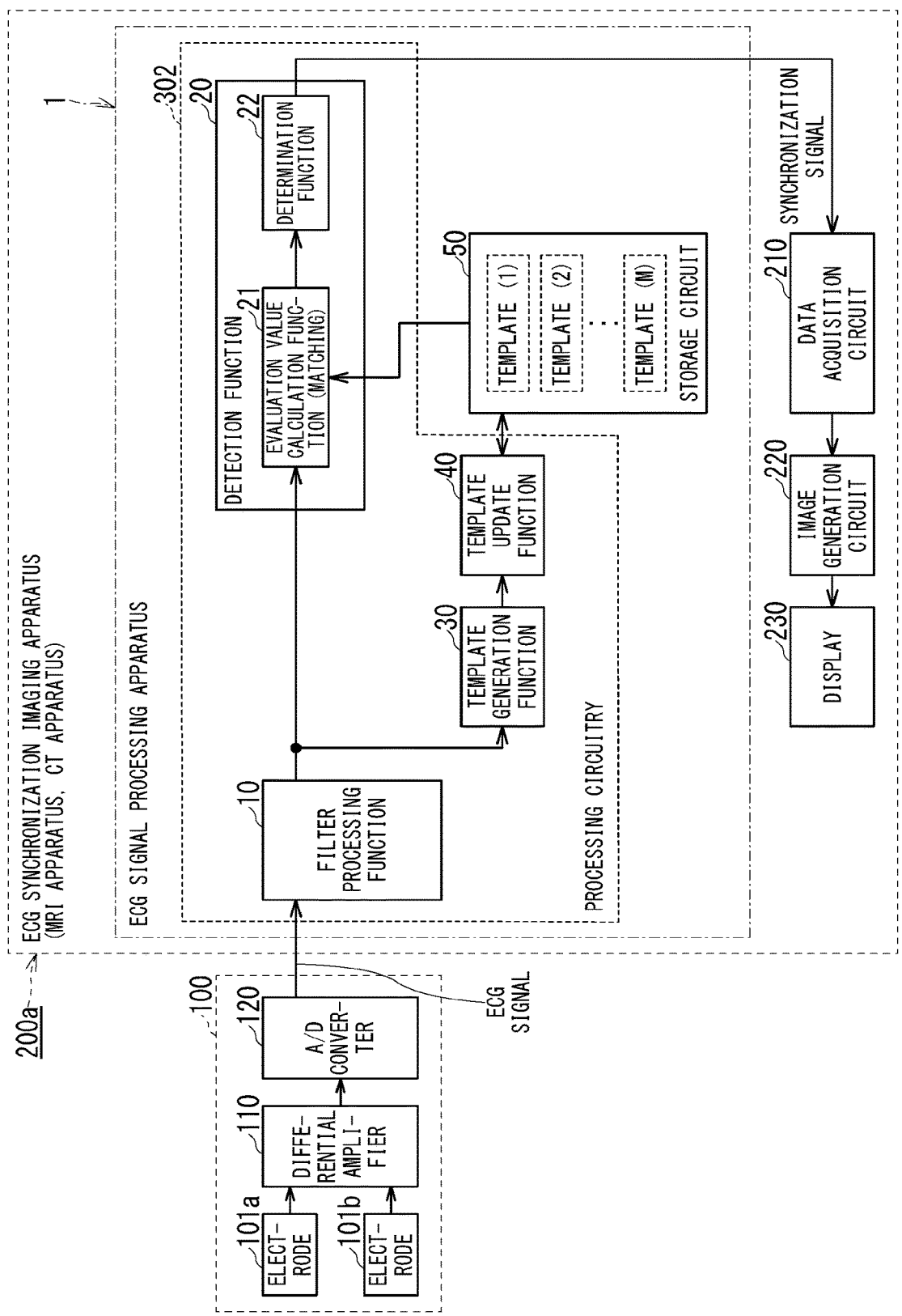
FIG. 18 is a functional block diagram showing an example of configuration in which an ECG synchronization imaging apparatus includes an ECG signal processing apparatus of one of the embodiments.

FIG. 18 is a functional block diagram showing an example of configuration in which an ECG synchronization imaging apparatus 200a includes the ECG signal processing apparatus 1. The ECG synchronization imaging apparatus 200a includes a data acquisition circuit 210 configured to acquire imaging data from an object in synchronization with a synchronization signal and an image generation circuit 220 configured to generate an image of the object based on the acquired imaging data, and a display 230 configured to display the generated image, aside from the ECG signal processing apparatus 1 configured to sequentially generate synchronization signals. The ECG signal processing apparatus 1 included in the ECG synchronization imaging apparatus 200a may include configuration and performance of each of the ECG signal processing apparatuses 1a, 1b, and 1c of the second to fourth embodiments.

When the ECG synchronization imaging apparatus 200a is an MRI apparatus, the above-described data acquisition circuit 210 is configured of a static magnetic field magnet, a gradient coil, an RF coil, an RF transmission circuit, an RF reception circuit, and a sequence controller included in the MRI apparatus. In addition, a part of processing circuitry such as a processor included in a host computer of the MRI apparatus configures the above-described image generation circuit 220.

In the respective embodiments described above, examples in which the ECG signal processing apparatuses 1, 1a, 1b, and 1c are separate components independent of the electrocardiograph 100 have been explained. However, the electrocardiograph 100 may be included in each of the ECG signal processing apparatus 1, 1a, 1b, and 1c as an internal component.

Fifth Embodiment

In each of the above-described first to fourth embodiments, synchronization signals can be generated from ECG signals outputted from one or plural electrocardiographs 100. On the other hand, for example, a twelve-lead electrocardiograph outputs twelve-dimensional ECG signals such as twelve ECG signals I, II, III, aVR, aVL, aVF, V1, V2, V3, V4, V5, and V6, for example. Additionally, in the case of an electrocardiograph of four terminals, two or three (two-dimensional or three-dimensional) ECG signals are outputted, for example. Moreover, a vectorcardiogram uses two or three ECG signals generated from plural electrode signals, for example.

Figure 19:
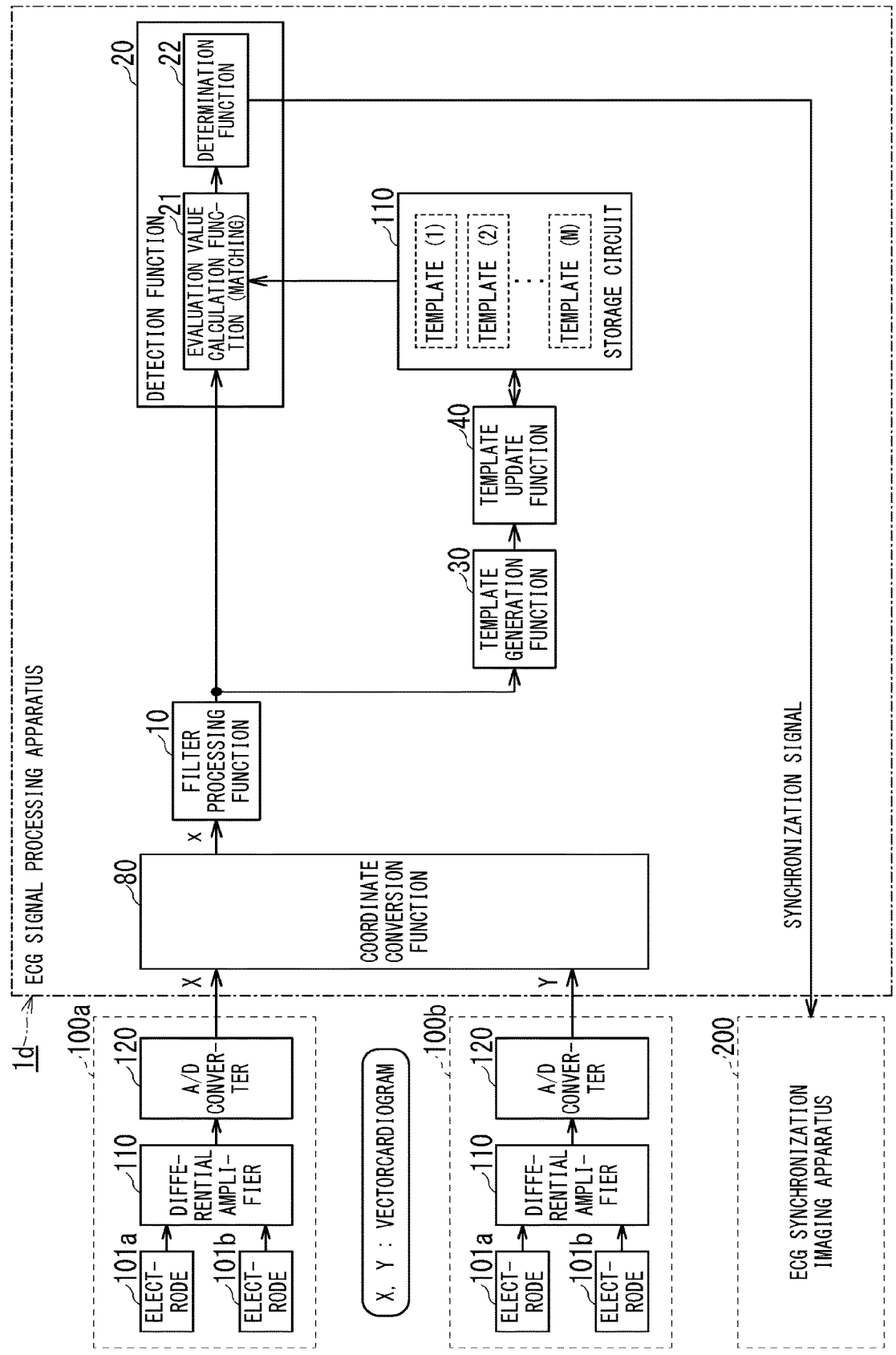
FIG. 19 is a functional block diagram showing an example of configuration of the ECG signal processing apparatus of the fifth embodiment.

The ECG signal processing apparatus 1d of the fifth embodiment detects an R-wave from a vectorcardiogram which uses plural ECG signals. FIG. 19 is a functional block diagram showing an example of configuration of the ECG signal processing apparatus 1d of the fifth embodiment.

Two electrocardiographs 100a and 100b are connected to the ECG signal processing apparatus 1d, for example. The electrocardiograph 100a includes electrodes 101a and 101b which are different from each other, and the electrocardiograph 100b includes electrodes 102a and 102b which are different from each other. An ECG signal outputted from the electrocardiograph 100a is defined as an ECG-induced first signal (X), and an ECG signal outputted from the electrocardiograph 100b is defined as an ECG-induced second signal (Y).

The configuration of the ECG signal processing apparatus 1d is the same as the ECG signal processing apparatus 1 of the first embodiment (see FIG. 4), except that the ECG signal processing apparatus 1d further includes a coordinate conversion function 80. The coordinate conversion function 80 is also implemented by the processing circuitry 302 (see FIG. 4).

Figure 20A:
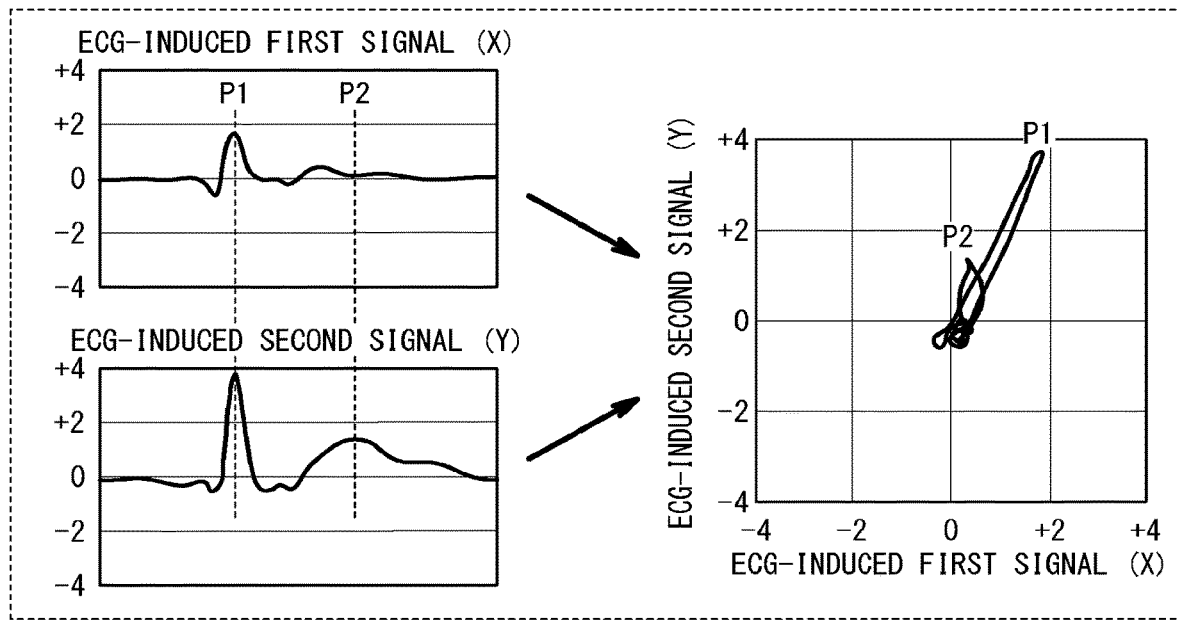
FIG. 20A and FIG. 20B are explanatory diagrams showing a concept of a coordinate conversion function of the ECG signal processing apparatus of the fifth embodiment, using a vectorcardiogram as an example.
Figure 20B:
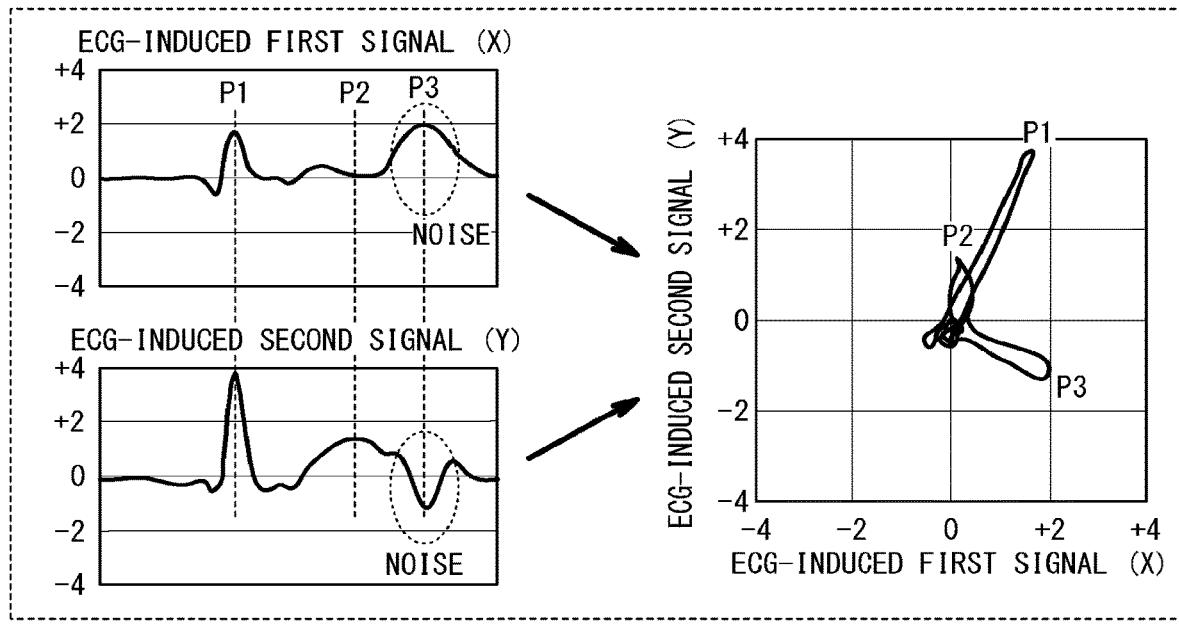
Figure 21:
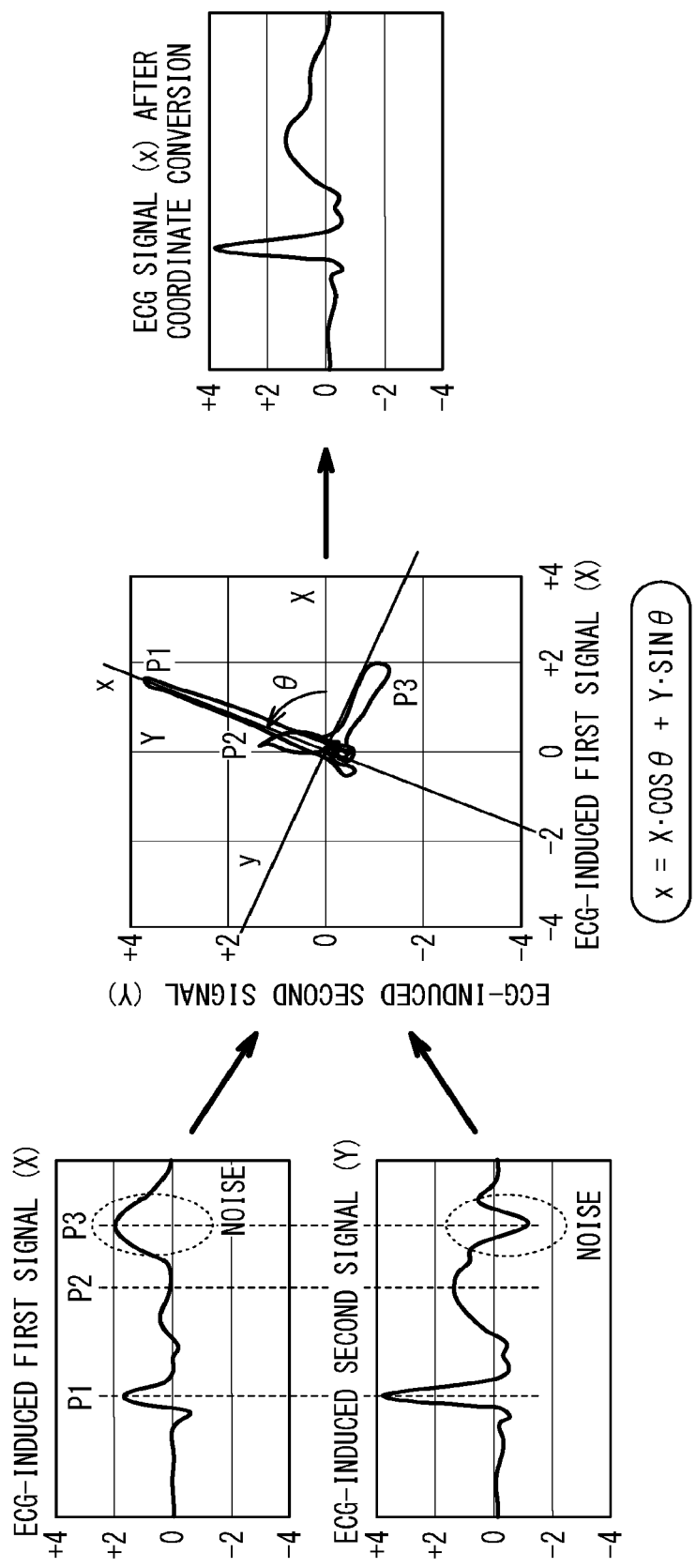
FIG. 21 is another explanatory diagram showing the concept of the coordinate conversion function of the ECG signal processing apparatus of the fifth embodiment, using a vectorcardiogram as an example.

FIG. 20A, FIG. 20B and FIG. 21 are explanatory diagrams showing a concept of the coordinate conversion function 80 by using a vectorcardiogram outputting an ECG-induced first signal (X) and an ECG-induced second signal (Y) as an example.

The upper chart and lower chart on the left side of FIG. 20A shows an example of a waveform of an ECG-induced first signal (X) and an example of a waveform of an ECG-induced second signal (Y), respectively. In the upper and lower charts on the left side of FIG. 20A, each horizontal axis indicates elapsed time and each vertical axis indicates amplitude. The chart on the right side of FIG. 20A obtained by plotting amplitude of an ECG-induced first signal (X) on the X axis (i.e., horizontal axis) and plotting amplitude of an ECG-induced second signal (Y) on the Y axis (i.e., vertical axis) along elapsed time. Hereinafter, this chart on the right side of FIG. 20A is referred to as a vector plotted graph.

FIG. 20A shows waveforms in a state where noise does not exist, e.g., a state where an object is outside an MRI apparatus. In the state where noise does not exist, there is a correlation between an ECG-induced first signal (X) and an ECG-induced second signal (Y). Therefore, the shape of the R-wave at the position P1 has its strong peak in an obliquely right direction from the origin in the vector plotted graph. In addition, the T-wave at the position P2 is also inclined to have its peak in the same direction as that of the R-wave.

By contrast, FIG. 20B shows waveforms in a state where noise exists, e.g., a state where an object is inside a gantry of an MRI apparatus and is subjected to a strong static magnetic field. In this state, as shown in the upper and lower charts on the left side of FIG. 20B, an ECG-induced first signal (X) and an ECG-induced second signal (Y) become susceptible to noise. For example, noise is superimposed at the position P3. In general, correlation of noise between an ECG-induced first signal (X) and an ECG-induced second signal (Y) is different from correlation of an R-wave between an ECG-induced first signal (X) and an ECG-induced second signal (Y). Therefore, in the vector plotted graph on the right side of FIG. 20B, the noise corresponding to the position P3 has its peak in a direction different from the peak direction of the R-wave whose peak is at the position P1. For example, the noise corresponding to the position P3 may have its peak in the direction approximately orthogonal to the peak direction of the R-wave.

In the fifth embodiment, a specific waveform such as an R-wave is more robustly detected by using the above-described characteristics of a vectorcardiogram. Specifically, an ECG-induced first signal (X) and an ECG-induced second signal (Y) are subjected to coordinate conversion and projected in the peak direction of an R-wave on a vector plotted graph by the coordinate conversion function 80.

FIG. 21 is an explanatory diagram showing the concept of the coordinate conversion function 80. The upper and lower charts in the left side of FIG. 21 are the same as those on the left side of FIG. 20A and FIG. 20B. The middle part of FIG. 21 is also the same vector plotted graph as the right side of FIG. 20B, except that the tilted angle θ of the peak direction of an R-wave is added. The right side of FIG. 21 shows an ECG signal (x) after coordinate conversion as described below.

First, the peak direction of an R-wave in a state where noise does not exist is assumed to be tilted from the X axis of an X-Y coordinate system by an angle θ. The coordinate conversion function 80 performs coordinate conversion on an ECG-induced first signal (X) and an ECG-induced second signal (Y) by rotating them by the angle θ, e.g., by using the following formulas.

$$x = X^* \cos(\theta) + Y^* \sin(\theta) \quad \text{Formula (4)}$$

$$y = -X^* \sin(\theta) + Y^* \cos(\theta) \quad \text{Formula (5)}$$

As a result, when the peak direction of noise is orthogonal to the peak direction of an R-wave as an example, the ECG signal (x) after the coordinate conversion becomes a signal in which noise is reduced as shown in the right part of FIG. 21.

The angle θ necessary for the coordinate conversion can be determined by (a) acquiring an ECG-induced first signal (X) and an ECG-induced second signal (Y) in a state where noise does not exist (e.g., a state where an object is outside an MRI apparatus) and (b) calculating the peak direction of an R-wave on a vector plotted graph.

The processing to be performed on the ECG signal (x) after the coordinate conversion is the same as that in the first to fourth embodiments. According to the ECG signal processing apparatus 1*d* of the fifth embodiment as mentioned above, a vectorcardiogram can be applied to each of the ECG signal processing apparatuses 1, 1*a*, 1*b*, and 1*c* of the first to fourth embodiments and influence of noise can be further reduced.

(Modification of Fifth Embodiment)

Figure 22:
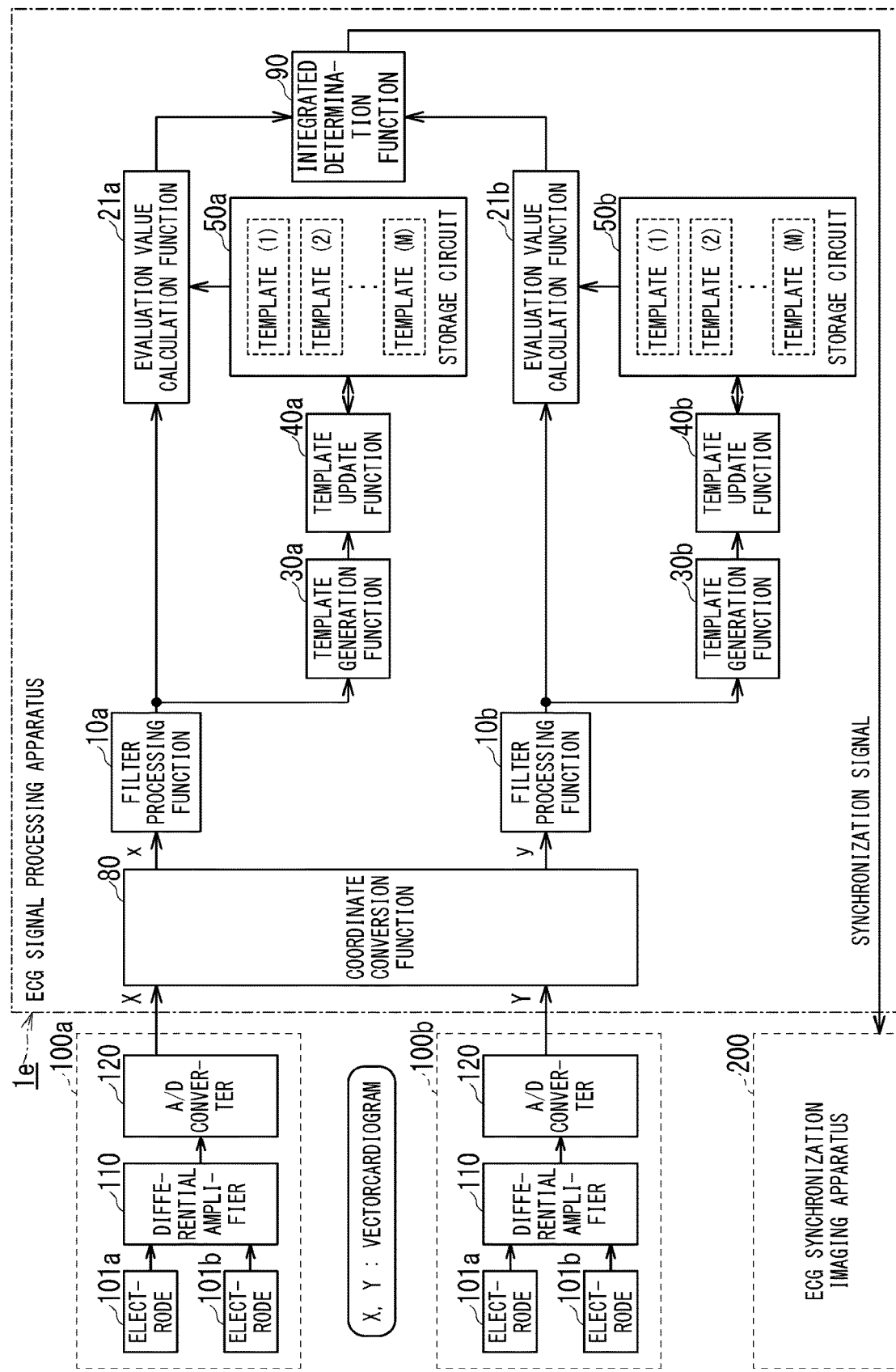
FIG. 22 is a functional block diagram showing an example of configuration of the ECG signal processing apparatus as a modification of the fifth embodiment.

FIG. 22 is a functional block diagram showing an example of configuration of the ECG signal processing apparatus 1*e* as a modification of the fifth embodiment. The configuration shown in FIG. 19 applies the processing of the first to fourth embodiments to one of the two ECG signals after coordinate conversion, i.e., to an ECG signal (x) obtained by the formula (4).

On the other hand, the ECG signal processing apparatus 1*e* of the modification of the fifth embodiment applies the processing of the first to fourth embodiments to plural ECG signals after the coordinate conversion, in parallel. For example, the processing of the first to fourth embodiments are applied to both of an ECG signal (x) obtained by the formula (4) and an ECG signal (y) obtained by the formula (5), in parallel. That is, the modification of the fifth embodiment includes two filter processing functions 10*a* and 10*b*, two template generation functions 30*a* and 30*b*, two template update functions 40*a* and 40*b*, two evaluation calculation functions 21*a* and 21*b*, and two storage circuits 50*a* and 50*b*. In this case, two evaluation values are calculated by two evaluation value calculation functions 21*a* and 21*b*, and these two evaluation values are inputted to an integrated determination function 90, as shown in FIG. 22.

The integrated determination function 90 is also implemented by the processing circuitry 302. The integrated determination function 90 detects an R-wave by (a) calculating a weighted average of the two evaluation values, for example, and (b) performing threshold processing on the weighted average with the use of a predetermined threshold value. Then, the integrated determination function 90 generates a synchronization signal based on the detected R-wave.

Incidentally, as mentioned above, many of synchronization signals used for synchronization imaging by an MRI apparatus are generated from ECG signals. Although an ECG signal is one of biosignals relevant to a heartbeat, the biosignals relevant to a heartbeat includes other signals such as a pulse wave signal and a cardiac sound signal aside from an ECG signal. In the ECG signal processing apparatus of each of the above-described embodiments, heartbeat synchronization signals can be generated by using biosignals relevant to a heartbeat such as pulse wave signals and cardiac sound signals for input signals, instead of using ECG signals. In this case, "ECG signal processing apparatus", "ECG signal processing method", and "ECG synchronization imaging apparatus" in the above-described explanation should be replaced with "signal processing apparatus", "signal processing method", and "heartbeat synchronization imaging apparatus", respectively. Further, in this case, "ECG signal", "ECG synchronization signal", and "ECG synchronization imaging" in the above-described explanation should be replaced with "biosignal relevant to a heartbeat", "heartbeat synchronization signal", and "heartbeat synchronization imaging", respectively.

According to the ECG signal processing apparatus of at least one of the above-described embodiments, an R-wave included in an ECG signal can be more robustly detected even if large noise is superimposed on an ECG signal during imaging and the like. Moreover, even if an abnormal waveform is included in an ECG signal, such an abnormal waveform can also be detected according to the ECG signal processing apparatus of at least one of the above-described embodiments. As a result, an imaging apparatus configured to perform ECG synchronization imaging can be supplied with synchronization signals stably and infallibly.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A signal processing apparatus comprising:
a storage circuit; and
processing circuitry configured to
  (a) generate two or more waveform templates for detecting an R-wave included in an electrocardiogram (ECG) signal, based on two or more waveforms acquired from a single biosignal sensor,
  (b) store the two or more waveform templates in the storage circuit,
  (c) sequentially generate a new waveform template, by extracting a part of the waveform of the ECG signal inputted time-sequentially,
  (d) calculate a similarity value between the new waveform template and each of the waveform templates stored in the storage circuit,
  (e) update the waveform templates stored in the storage circuit by storing the new waveform template when the similarity value is smaller than a predetermined value,
  (f) detect the R-wave by performing matching processing between a waveform of the ECG signal inputted time-sequentially and each of the two or more waveform templates, and
  (g) generate a synchronization signal for performing heartbeat synchronization imaging based on the R-wave.

2. The signal processing apparatus according to claim 1, wherein the processing circuitry is configured to
  (a) calculate two or more evaluation values respectively corresponding to the two or more waveform templates, by performing matching processing between the waveform of the ECG signal and the two or more waveform templates, and
  (b) detect the R-wave by comparing an integrated evaluation value obtained from the calculated two or more evaluation values with a predetermined threshold value.

3. The signal processing apparatus according to claim 2, wherein the two or more evaluation values are respective two or more difference evaluation values based on differences between the waveform of the ECG signal and the two or more waveform templates, and the integrated evaluation value is a smallest value among the two or more difference evaluation values.

4. The signal processing apparatus according to claim 1, wherein the processing circuitry is configured to (a) monitor an operating state of an external imaging apparatus connected to the signal processing apparatus, and
  (b) determine whether the processing circuitry generates the two or more waveform templates, depending on the operating state of the external imaging apparatus.

5. The signal processing apparatus according to claim 4, wherein the external imaging apparatus is an MRI apparatus, and
wherein the processing circuitry is configured to
  (a) monitor an operating state of the MRI apparatus,
  (b) update the waveform templates in a period during which the MRI apparatus does not perform imaging, and
  (c) hold the waveform templates, which are stored in the storage circuit immediately before start of imaging performed by the MRI apparatus, without updating the waveform templates, during the imaging performed by the MRI apparatus.

6. The signal processing apparatus according to claim 1, wherein the processing circuitry is configured to
  (a) enhance the R-wave in the ECG signal by performing filter processing, and
  (b) generate the waveform templates from the ECG signal in which the R-wave is enhanced by the filter processing.

7. The signal processing apparatus according to claim 6, wherein the processing circuitry is configured to
  (a) generate a high-frequency enhanced ECG signal by performing a first filter processing for enhancing a high-frequency band on the ECG signal,
  (b) generate a band-enhanced ECG signal by performing a second filter processing for enhancing a specific frequency band on the ECG signal,
  (c) generate two or more first waveform templates from the high-frequency enhanced ECG signal,
  (d) generate two or more second waveform templates from the band-enhanced ECG signal,
  (e) store the first waveform templates and the second waveform templates in the storage circuit,
  (f) calculate a first evaluation value by performing matching processing between a waveform of the high-frequency enhanced ECG signal and each of the first waveform templates,
  (g) calculate a second evaluation value by performing matching processing between a waveform of the band-enhanced ECG signal and each of the second waveform templates, and
  (h) detect the R-wave based on the first evaluation value and the second evaluation value.

8. The signal processing apparatus according to claim 6, further comprising a second storage circuit configured to store at least one fixed template which is preliminarily generated,
wherein the processing circuitry is configured to detect the R-wave based on (a) a fixed template evaluation value calculated by performing matching processing between the waveform of the inputted ECG signal and the at least one fixed template stored in the second storage circuit and (b) an evaluation value calculated by performing matching processing between the waveform of the inputted ECG signal and each of the waveform templates stored in the storage circuit.

9. The signal processing apparatus according to claim 1, wherein the ECG signal is a vectorcardiogram which includes two or more ECG signals; and the processing circuitry is configured to perform coordinate conversion on the vectorcardiogram and to generate the synchronization signal from at least one of the ECG signals included in the vectorcardiogram subjected to the coordinate conversion.

10. An imaging apparatus comprising:

a storage circuit;

processing circuitry configured to
- (a) generate two or more waveform templates for detecting a an R-wave included in an electrocardiogram (ECG) signal, based on a waveform of the ECG signal,
- (b) store the two or more waveform templates in the storage circuit,
- (c) sequentially generate a new waveform template, by extracting a part of the waveform of the ECG signal inputted time-sequentially,
- (d) calculate a similarity value between the new waveform template and each of the waveform templates stored in the storage circuit,
- (e) update the waveform templates stored in the storage circuit by storing the new waveform template when the similarity value is smaller than a predetermined value,
- (f) detect the R-wave by performing matching processing between a waveform of the ECG signal inputted time-sequentially and each of the two or more waveform templates, and
- (g) generate a synchronization signal for performing heartbeat synchronization imaging based on the R-wave;

a data acquisition circuit configured to acquire imaging data form an object in synchronization with the synchronization signal; and an image generation circuit configured to generate an image of the object based on the imaging data.

11. The imaging apparatus according to claim 10, wherein the imaging apparatus is an MRI apparatus.

12. The imaging apparatus according to claim 10, wherein the ECG signal is a vectorcardiogram which includes two or more ECG signals; and the processing circuitry is configured to perform coordinate conversion on the vectorcardiogram and to generate the synchronization signal from at least one of the ECG signals included in the vectorcardiogram subjected to the coordinate conversion.

13. A signal processing method comprising:

generating two or more waveform templates for detecting an R-wave included in an electrocardiogram (ECG) signal, based on two or more waveforms acquired from a single biosignal sensor;

storing the two or more waveform templates;

sequentially generating a new waveform template, by extracting a part of the waveform of the ECG signal inputted time-sequentially, calculating a similarity value between the new waveform template and each of the stored waveform templates, updating the stored waveform templates by storing the new waveform template when the similarity value is smaller than a predetermined value, detecting the R-wave by performing matching processing between a waveform of the ECG signal inputted time-sequentially and each of the two or more waveform templates; and generating a synchronization signal for performing heartbeat synchronization imaging based on the R-wave.

14. The signal processing method according to claim 13, wherein the ECG signal is a vectorcardiogram which includes two or more ECG signals; and the generating the synchronization signal comprises (a) performing coordinate conversion on the vectorcardiogram and (b) generating the synchronization signal from at least one of the ECG signals included in the vectorcardiogram subjected to the coordinate conversion.

* * * * *